(12) United States Patent
Klein et al.

(10) Patent No.: US 9,833,783 B1
(45) Date of Patent: Dec. 5, 2017

(54) FLUID RETAINER CARTRIDGE ASSEMBLY AND METHOD FOR UTILIZING THE SAME

(71) Applicant: Neogen Corporation, Lansing, MI (US)

(72) Inventors: Frank Eric Klein, Howell, MI (US); Andrew John Wheeler, Hollis Center, ME (US); Andrew John DenHartigh, Lansing, MI (US); William Hoerner, Lansing, MI (US); Damon Borich, Austin, TX (US); Zwckxally Obregon, Cedar Creek, TX (US); Andrea Grbavac, Austin, TX (US); Karen Borich, Austin, TX (US); Alejandro Silveyra, Austin, TX (US)

(73) Assignee: NEOGEN CORPORATION, Lansing, MI (US)

( * ) Notice: Subject to any disclaimer, the term of this patent is extended or adjusted under 35 U.S.C. 154(b) by 0 days.

(21) Appl. No.: 15/488,627

(22) Filed: Apr. 17, 2017

Related U.S. Application Data

(60) Provisional application No. 62/439,568, filed on Dec. 28, 2016.

(51) Int. Cl.
| | |
|---|---|
| *G01N 1/38* | (2006.01) |
| *G01N 1/28* | (2006.01) |
| *B01L 3/00* | (2006.01) |

(52) U.S. Cl.
CPC ............... *B01L 3/508* (2013.01); *G01N 1/38* (2013.01); *B01L 2200/0621* (2013.01);
(Continued)

(58) Field of Classification Search
CPC .. G01N 1/38; G01N 1/28; B01L 3/508; B01L 3/502; B01L 3/50
(Continued)

(56) References Cited

U.S. PATENT DOCUMENTS

| | | |
|---|---|---|
| 657,080 A | 9/1900 | Belden |
| 4,099,920 A | 7/1978 | Heiss |

(Continued)

FOREIGN PATENT DOCUMENTS

| | | |
|---|---|---|
| EP | 0155747 A1 | 10/1985 |
| EP | 0299428 B2 | 1/2004 |

(Continued)

OTHER PUBLICATIONS

Technical Specification of Neogen AccuScan II Reader, Version 07.03.2006, 5 pages.
(Continued)

*Primary Examiner* — Christine T Mui

(74) *Attorney, Agent, or Firm* — Honigman Miller Schwartz and Cohn LLP; Douglas H. Siegel; Jonathan P. O'Brien

(57) ABSTRACT

A fluid retainer cartridge assembly is disclosed. The fluid retainer cartridge assembly includes a base portion and a cap portion. The base portion defines a plurality of implement-receiving channels. The cap portion is removably-connected to the base portion. The cap portion defines a fluid-receiving void that is fluidly-divided into an upstream fluid-receiving void and a downstream fluid-receiving void by a flange of the base portion that is disposed within the fluid-receiving void of the cap portion. The upstream fluid-receiving void is in fluid communication with the downstream fluid-receiving void by a fluid-flow passage formed by the flange of the base portion. A method is also disclosed.

17 Claims, 16 Drawing Sheets

(52) U.S. Cl.
CPC . *B01L 2300/042* (2013.01); *B01L 2300/0681* (2013.01); *B01L 2300/087* (2013.01)

(58) Field of Classification Search
USPC .......... 422/939, 940, 946, 50, 68.1; 436/180
See application file for complete search history.

(56) References Cited

U.S. PATENT DOCUMENTS

| | | | |
|---|---|---|---|
| 4,353,868 A | 10/1982 | Joslin et al. | |
| 4,409,988 A | 10/1983 | Greenspan | |
| 4,770,853 A | 9/1988 | Bernstein | |
| 4,857,454 A | 8/1989 | Freundlich et al. | |
| 4,920,046 A | 4/1990 | McFarland et al. | |
| 5,108,896 A | 4/1992 | Philo et al. | |
| 5,158,869 A | 10/1992 | Pouletty et al. | |
| 5,168,908 A | 12/1992 | Boyum | |
| 5,223,401 A | 6/1993 | Foltz et al. | |
| 5,238,649 A | 8/1993 | Nason | |
| 5,424,220 A | 6/1995 | Goerlach-Graw et al. | |
| 5,726,010 A | 3/1998 | Clark | |
| 5,726,013 A | 3/1998 | Clark | |
| 5,766,962 A | 6/1998 | Childs et al. | |
| D405,539 S | 2/1999 | Poissant et al. | |
| 5,874,216 A | 2/1999 | Mapes | |
| 5,962,339 A | 10/1999 | Midgely | |
| 5,985,675 A | 11/1999 | Charm et al. | |
| D419,439 S | 1/2000 | Markovsky et al. | |
| 6,124,585 A | 9/2000 | Riedel et al. | |
| 6,136,610 A | 10/2000 | Polito et al. | |
| 6,207,369 B1 | 3/2001 | Wohlstadter et al. | |
| 6,319,466 B1 | 11/2001 | Markovsky et al. | |
| 6,372,516 B1* | 4/2002 | Sun ..................... | B01L 3/5023 422/408 |
| 6,514,769 B2* | 2/2003 | Lee ..................... | B01L 3/5023 422/110 |
| 6,524,804 B2 | 2/2003 | Degelaen | |
| 6,663,833 B1 | 12/2003 | Stave et al. | |
| 7,044,919 B1 | 5/2006 | Catt et al. | |
| 7,097,983 B2 | 8/2006 | Markovsky et al. | |
| 7,172,897 B2 | 2/2007 | Blackburn et al. | |
| 7,267,799 B1 | 9/2007 | Borich et al. | |
| 7,462,464 B1 | 12/2008 | Langeveld et al. | |
| 7,558,259 B2 | 7/2009 | Eden | |
| 7,785,899 B2 | 8/2010 | Saul et al. | |
| 7,803,322 B2 | 9/2010 | Borich et al. | |
| 7,879,624 B2 | 2/2011 | Sharrock | |
| 7,897,365 B2 | 3/2011 | Salter et al. | |
| 8,005,280 B2 | 8/2011 | Mott et al. | |
| 8,106,155 B2 | 1/2012 | Degelaen et al. | |
| 8,446,463 B2 | 5/2013 | Fleming et al. | |
| 8,470,609 B2* | 6/2013 | Chen ..................... | B01L 3/5023 422/420 |
| 8,475,731 B2 | 7/2013 | Abraham et al. | |
| 8,476,064 B2 | 7/2013 | Salter et al. | |
| 8,524,501 B2 | 9/2013 | Adams | |
| 8,698,881 B2 | 4/2014 | Fleming et al. | |
| 8,848,988 B2 | 9/2014 | Plickert et al. | |
| 8,883,489 B2 | 11/2014 | Pang et al. | |
| 9,008,373 B2 | 4/2015 | Markovsky et al. | |
| 9,052,297 B2 | 6/2015 | Jakubowicz et al. | |
| 9,057,724 B2 | 6/2015 | Saul | |
| 9,063,137 B2 | 6/2015 | Saul et al. | |
| 9,488,657 B2 | 11/2016 | Graham et al. | |
| 2002/0127623 A1 | 9/2002 | Minshull et al. | |
| 2002/0150501 A1 | 10/2002 | Robertson et al. | |
| 2003/0207442 A1 | 11/2003 | Markovsky et al. | |
| 2004/0096356 A1 | 5/2004 | Degelaen et al. | |
| 2005/0052646 A1 | 3/2005 | Wohlstadter et al. | |
| 2005/0112024 A1 | 5/2005 | Guo et al. | |
| 2005/0220668 A1 | 10/2005 | Coville | |
| 2005/0227370 A1 | 10/2005 | Ramel et al. | |
| 2006/0066850 A1 | 3/2006 | Kimura | |
| 2006/0115896 A1 | 6/2006 | Wong et al. | |
| 2006/0292036 A1 | 12/2006 | Gould et al. | |
| 2007/0110623 A1 | 5/2007 | Liu | |
| 2008/0019887 A1 | 1/2008 | Lohmann et al. | |
| 2008/0031779 A1 | 2/2008 | Polito et al. | |
| 2008/0081002 A1 | 4/2008 | Petruno et al. | |
| 2008/0295831 A1 | 12/2008 | Svehaug et al. | |
| 2009/0098022 A1 | 4/2009 | Tokhtuev et al. | |
| 2009/0269760 A1 | 10/2009 | Samadpour | |
| 2010/0012490 A1 | 1/2010 | Hsu | |
| 2010/0055721 A1 | 3/2010 | Lambert et al. | |
| 2010/0151460 A1 | 6/2010 | Winther | |
| 2010/0267049 A1 | 10/2010 | Rutter et al. | |
| 2011/0171754 A1 | 7/2011 | Redmond et al. | |
| 2011/0255756 A1 | 10/2011 | Harris et al. | |
| 2012/0220051 A1 | 8/2012 | Yin et al. | |
| 2013/0006146 A1 | 1/2013 | Vemalarajah | |
| 2013/0280698 A1 | 10/2013 | Propper et al. | |
| 2014/0057362 A1 | 2/2014 | Markovsky et al. | |
| 2014/0120556 A1 | 5/2014 | Moll et al. | |
| 2014/0154792 A1 | 6/2014 | Moyniham et al. | |
| 2014/0271362 A1 | 9/2014 | Markovsky et al. | |
| 2014/0334980 A1 | 11/2014 | Graham et al. | |
| 2015/0140681 A1 | 5/2015 | Meng et al. | |
| 2015/0276613 A1 | 10/2015 | Markovsky | |
| 2016/0103075 A1 | 4/2016 | Borich et al. | |
| 2016/0187239 A1 | 6/2016 | Givens et al. | |
| 2016/0310948 A1 | 10/2016 | Nowakowski et al. | |

FOREIGN PATENT DOCUMENTS

| | | | |
|---|---|---|---|
| EP | 1095270 B2 | 11/2010 | |
| GB | 2460956 B | 11/2010 | |
| GB | 2483077 A | 2/2012 | |
| WO | 2006073500 A2 | 7/2006 | |
| WO | 2009/038798 A1 | 3/2009 | |
| WO | 2011/140476 A1 | 11/2011 | |
| WO | 2012027583 A2 | 3/2012 | |
| WO | 2012145730 A2 | 10/2012 | |
| WO | 2013/116847 A1 | 8/2013 | |
| WO | 2014126918 A1 | 8/2014 | |
| WO | WO 2015/017591 A1 * | 2/2015 | ............ G01N 33/53 |
| WO | 2016203019 A1 | 12/2016 | |

OTHER PUBLICATIONS

2014 Neogen Corporation's AccuScan Pro User Manual, 14 pages.
2012 Neogen Corporation's Product Brochure for AccuScan Pro, 1 page.
Neogen Corporation's User's Guide for Reveal AccuScan III, Nov. 2010, 9 pages.
Neogen Corporation's presentation regarding AccuScan Gold, Nov. 2015, 21 pages.
2015 Neogen Corporation's AccuScan Gold Manual, 12 pages.
Neogen Corporation's user guide presentation regarding AccuScan Pro, Aug. 2012, 13 pages.
Neogen Corporation's product and directions for use regarding Reveal Q+ product line, 2014, 2 pages.
2014 Neogen Corporation's Product Brochure for AccuScan Gold, 2 pages.
Photographs of Accuscan Gold device, 4 pages, publicly available before Apr. 17, 2016.
Photographs of Accuscan Pro device, 4 pages, publicly available before Apr. 17, 2016.
Charm EZ brochure, Jun. 2015, 4 pages.
Charm EZ-M brochure, Sep. 2015, 4 pages.
Charm EZ Lite brochure, May 2015, 2 pages.
IDEXX SNAPshot DSR Reader Operator's Guide, 2008, 100 pages.
Integrated EZ Split Key Cup, Product Training Procedures, 2012, 24 pages.
Ploughshare Biodetection device, believed to be publicly available before Apr. 17, 2016, 1 page.
Envirologix QuickComb product insert, Rev. Jan. 7, 2016, 6 pages.
2007 Neogen Corporation's Product Brochure for Reveal AccuScan III, 2 pages.
Reveal Sciences CareType™ Analysis System, 2 pages, 2009.

(56) References Cited

OTHER PUBLICATIONS

Alexeter Techologies LLC "The Defender TSR™", 2 pages, believed to be publicly available before Apr. 17, 2016.
VICAM's Vertu Lateral Flow Reader, 1 page, believed to be publicly available before Apr. 17, 2016.
ESEQuant Lateral Flow Reader, 3 pages, believed to be publicly available before Apr. 17, 2016.
Aleve™ Reader, 7 pages, [date unknown].
Siemens Medical Solutions USA, Inc.'s "Clinitek Status+ Urine Analyzer", 4 pages, believed to be publicly available before Apr. 17, 2016.
Skannex BioAssay Reader Systems™ SkanMulti, 2 pages, believed to be publicly available before Apr. 17, 2016.
Sep. 6, 2017 International Search Report and Written Opinion for PCT/US2017/027863.
Aug. 8, 2017 International Search Report and Written Opinion for PCT/US2017/027890.

* cited by examiner

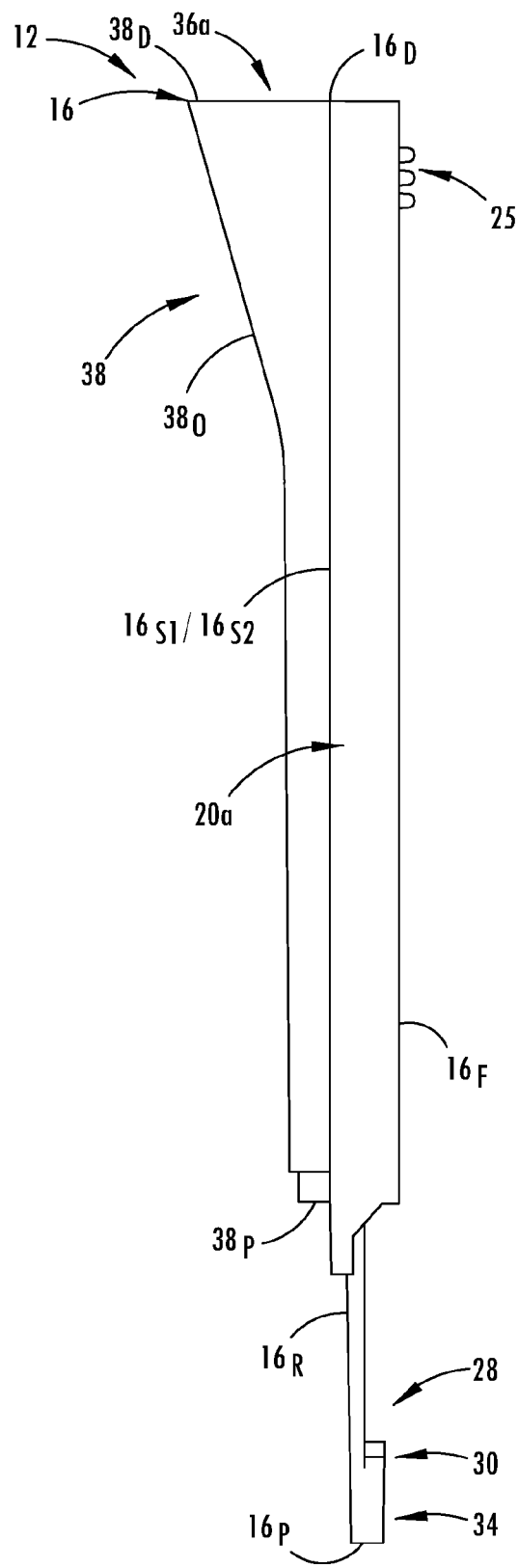
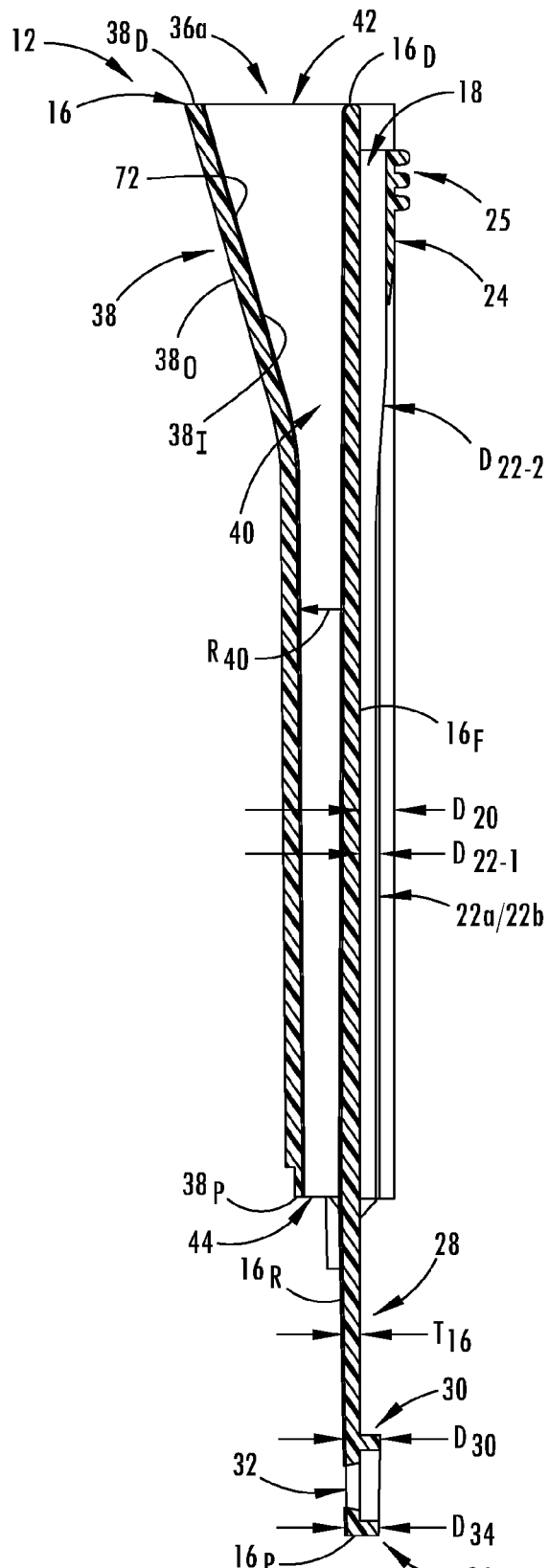
FIG. 6  FIG. 7

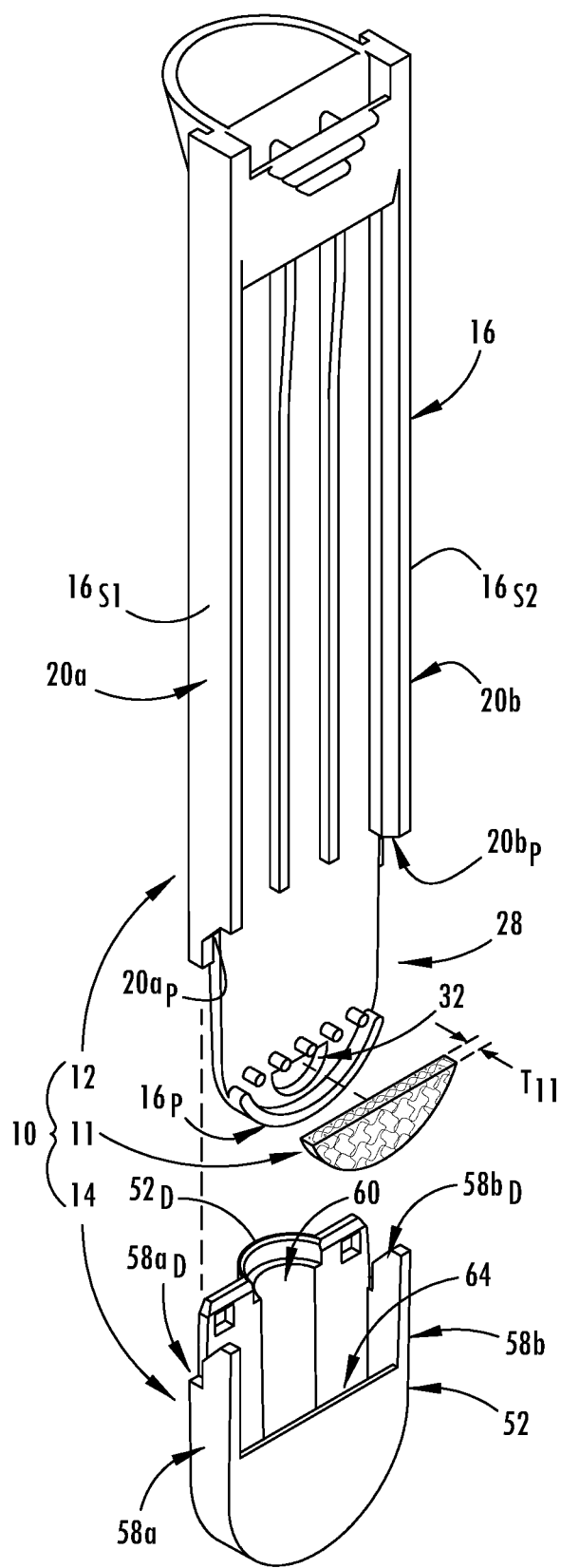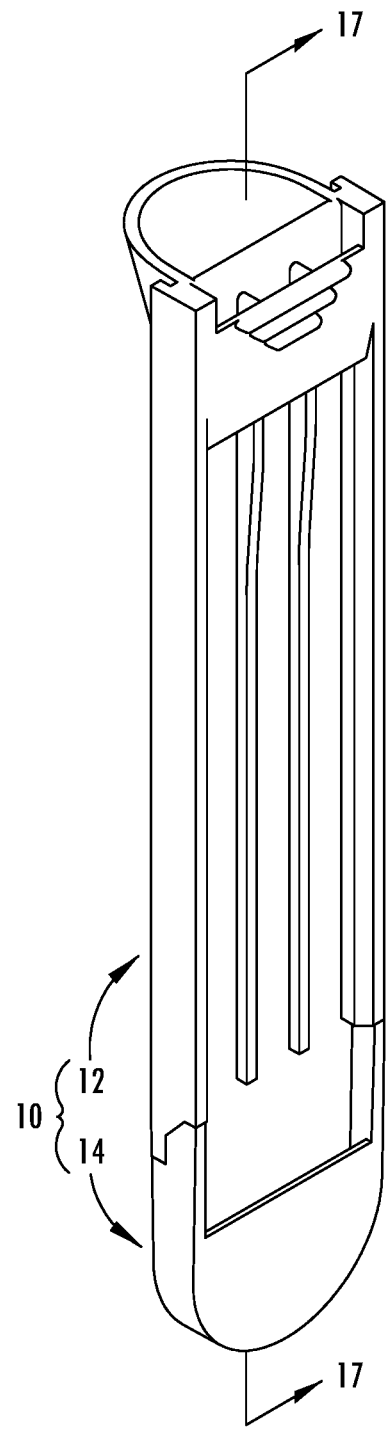
FIG. 14A
FIG. 14B

FLUID RETAINER CARTRIDGE ASSEMBLY AND METHOD FOR UTILIZING THE SAME

CROSS-REFERENCE TO RELATED APPLICATIONS

This U.S. Patent Application claims priority to U.S. Provisional Application 62/439,568 filed on Dec. 28, 2016, the disclosure of which is considered part of the disclosure of this application and is hereby incorporated by reference in its entirety.

TECHNICAL FIELD

This disclosure relates to devices and methods for assaying test samples.

BACKGROUND

Fluid retainer cartridge assemblies are known. While existing fluid retainer cartridge assemblies perform adequately for their intended purpose, improvements to fluid retainer cartridge assemblies are continuously being sought in order to advance the arts.

SUMMARY

This section provides a general summary of the disclosure, and is not a comprehensive disclosure of its full scope or all of its features.

One aspect of the disclosure provides a fluid retainer cartridge assembly. The fluid retainer cartridge assembly includes a base portion and a cap portion. The base portion defines a plurality of implement-receiving channels. The cap portion is removably-connected to the base portion. The cap portion defines a fluid-receiving void that is fluidly-divided into an upstream fluid-receiving void and a downstream fluid-receiving void by a flange of the base portion that is disposed within the fluid-receiving void of the cap portion. The upstream fluid-receiving void is in fluid communication with the downstream fluid-receiving void by a fluid-flow passage formed by the flange of the base portion.

Implementations of the disclosure may include one or more of the following optional features. For example, the fluid retainer cartridge assembly also includes a fluid filter disposed adjacent the fluid-flow passage formed by the flange of the base portion.

In some implementations, the upstream fluid-receiving void is in fluid communication with an axial fluid conduit formed by: a fluid-flow passage formed, in part, by a rear surface of a body of the base portion; and a channel formed by a front surface of a body of the cap portion. The downstream fluid-receiving void is in fluid communication with the plurality of implement-receiving channels.

In some examples, the plurality of implement-receiving channels are further defined by: a first sidewall flange extending from the front surface of the body of the base portion; a second sidewall flange extending from the front surface of the body of the base portion; and at least one rib extending from the front surface of the body of the base portion and arranged between the first sidewall flange and the second sidewall flange.

In some implementations, the front surface of the body of the base portion further defines an implement distal end retainer portion that extends across a width of the base portion and connects the first sidewall flange to the second sidewall flange.

In some examples, the implement distal end retainer portion is defined by a distal end and a proximal end. The distal end of the implement distal end retainer portion is arranged at a distance away from the distal end surface of the body of the base portion for defining an access port.

In some implementations, the at least one rib includes a first rib and a second rib. The first rib is arranged between the first sidewall flange and the second rib. The second rib is arranged between the first rib and the second sidewall flange.

In some examples, the first sidewall flange is spaced apart from the first rib at a distance equal to a first portion of a width of the base portion for defining a first implement-receiving channel of the plurality of implement-receiving channels. The first rib is spaced apart from the second rib at a distance equal to a second portion of the width of the base portion for defining a second implement-receiving channel of the plurality of implement-receiving channels. The second rib is spaced apart from the second sidewall flange at a distance equal to a third portion of the width of the base portion for defining a third implement-receiving channel of the plurality of implement-receiving channels.

In some implementations, the front surface of the body of the base portion defined by the flange includes a plurality of projections arranged in a row at a length away from a proximal end surface of the body of the base portion.

In some examples, the plurality of projections includes: a first projection aligned with the first implement-receiving channel; a second projection aligned with the first rib; a third projection aligned with the second implement-receiving channel; a fourth projection aligned with the second rib; and a fifth projection aligned with the third implement-receiving channel.

In some implementations, the fluid-flow passage is further defined by an inner surface of a funnel body that extends away from the rear surface of the base portion. Access to the fluid-flow passage is formed by an upstream opening and a downstream opening.

In some examples, the fluid-flow passage is defined by an arcuate channel having a radius extending between the inner surface of the funnel body and the rear surface of the base portion. The radius progressively increases near a distal surface of the funnel body such that the upstream opening forms a larger opening than that of the downstream opening.

In some implementations, a rear surface of a body of the base portion forms a cap-retainer portion defined by a pair of protrusions including a first protrusion and a second protrusion. Each of the first protrusion and the second protrusion includes a ramp surface and latch surface.

In some examples, a body of the cap portion defines a pair of protrusion-receiving passages that extend through the thickness of the body of the cap portion. The pair of protrusion-receiving passages include a first protrusion-receiving passage and a second protrusion-receiving passage. The first protrusion and the second protrusion are respectively arranged within the first protrusion-receiving passage and the second protrusion-receiving passage.

In some implementations, the fluid-receiving void of the cap portion is further defined by a flange-receiving housing including an implement proximal end retainer portion.

Another aspect of the disclosure provides a method. The method includes the steps of: arranging at least one implement in one implement-receiving channel of the plurality of implement-receiving channels of the fluid retainer cartridge assembly; pouring a fluid into the fluid-receiving void of the fluid retainer cartridge assembly such that the fluid: firstly enters the upstream fluid-receiving void then secondly enters the fluid-flow passage formed by the flange of the base portion of the fluid retainer cartridge assembly then thirdly enters the downstream fluid-receiving void for fluidly contacting the fluid with the at least one implement that is in fluid communication with the downstream fluid-receiving void.

Implementations of the disclosure may include one or more of the following optional features. For example, the at least one implement is a test strip assay and the fluid includes a chemical analyte that chemically reacts with the at least one test strip assay.

The details of one or more implementations of the disclosure are set forth in the accompanying drawings and the description below. Other aspects, features, and advantages will be apparent from the description and drawings, and from the claims.

DESCRIPTION OF DRAWINGS

The drawings described herein are for illustrative purposes only of selected configurations and not all possible implementations, and are not intended to limit the scope of the present disclosure.

FIG. 6 is a side view of the base portion of FIG. 2.

FIG. 7 is a cross-sectional view of the base portion according to line 7-7 of FIG. 2.

FIG. 14A is a front exploded view of the fluid retainer cartridge assembly of FIG. 1A.

FIG. 14B is a front assembled view of the fluid retainer cartridge assembly of FIG. 14A.

FIG. 19A is an enlarged view according to line 19A of FIG. 19.

FIG. 20A is an enlarged view according to line 20A of FIG. 20.

FIG. 21A is an enlarged view according to line 21A of FIG. 21.

Like reference symbols in the various drawings indicate like elements.

DETAILED DESCRIPTION

Figures 1A, 1B:
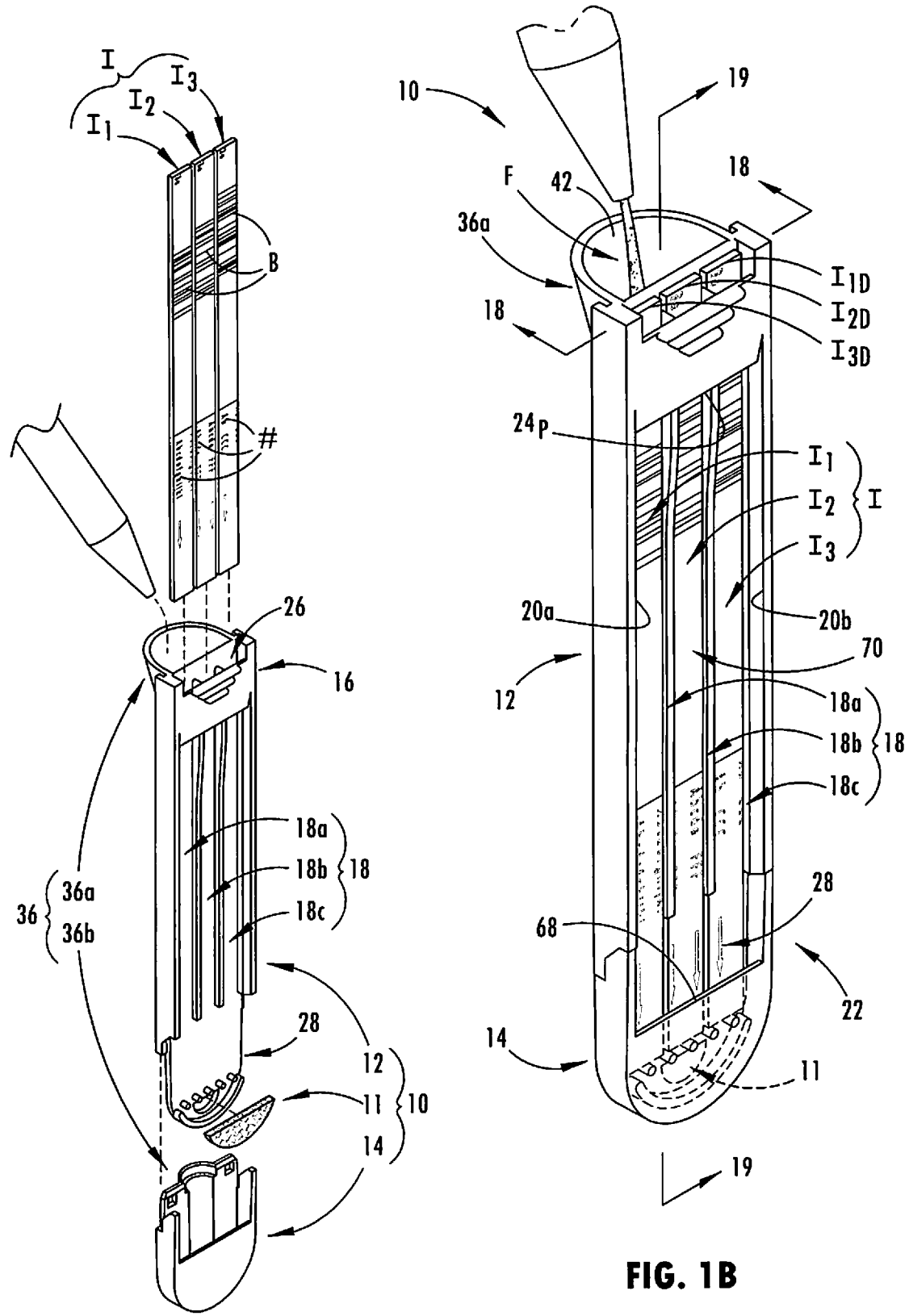
FIG. 1A is an exploded perspective view of a fluid retainer cartridge assembly and a plurality of implements positioned relative to the fluid retainer cartridge assembly.
FIG. 1B is an assembled perspective view of the fluid retainer cartridge assembly of FIG. 1A and the plurality of implements positioned within the fluid retainer cartridge assembly.

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

Referring to FIGS. 1A and 1B, a fluid retainer cartridge assembly is shown generally at 10. The fluid retainer cartridge assembly 10 includes a base portion 12 and a cap portion 14 that is fluidly-connected to the base portion 12. The fluid retainer cartridge assembly 10 may optionally include a fluid filter 11 that may be connected to the base portion 12.

As will be explained in greater detail in the following disclosure (at FIGS. 18-22), the base portion 12 and the cap portion 14 collectively retain at least one (e.g., three) implement I (see, e.g., FIGS. 1A-1B) while the base portion 12 guides an amount of fluid F, for example, raw milk (see, e.g., FIG. 1B) into a fluid-receiving void defined by the cap portion 14. If optionally included, the fluid filter 11 may filter the fluid F. Once the fluid F arrives in the fluid-receiving void of the cap portion 14, the fluid F contacts the at least one implement I. In an example, the at least one implement I may be a test strip assay and the fluid F may include a chemical analyte (e.g., a veterinary antibiotic, such as a beta-lactam or tetracycline) that chemically reacts with the at least one test strip assay I. In an example as seen in FIG. 1A, each implement $I_1$, $I_2$, $I_3$ of the plurality of implements I may include indicia, such as, for example, one or more of a barcode B, letters and/or numbers # or the like that may be read by an optical reader of an implement analyzing device (not shown) that can monitor, read and analyze the one or more implements I before, during or after being contacted with the fluid F.

Although an exemplary fluid F may include, for example, raw milk as described above, other fluids F may be interfaced with the fluid retainer cartridge assembly 10. For example, other exemplary fluids F may include, but is not limited to: blood, saliva, corn fluid or the like. Furthermore, the fluid F may be interfaced with the fluid retainer cartridge assembly 10 at any desirable temperature, such as, for example, room temperature, a temperature that is lower than room temperature (as a result of, for example, cooling or chilling the fluid F) or a temperature that is higher than room temperature (as a result of, for example, warming or heating the fluid F).

Each of the base portion 12 and the cap portion 14 may be formed from a thermoplastic or other material suitable for injection molding, such as, acrylonitrile butadiene styrene (ABS plastic). Other exemplary materials may include polypropylene, polystyrene, nylon, polycarbonate, and thermoplastics infused with polymers (e.g., graphite, carbon fibers, glass-reinforced) to enhance thermal conductivity. The thermoplastic material may promote, for example, sufficient heat transfer of heat from an external heating source in order to warm or heat the fluid F that is disposed within the fluid retainer cartridge assembly 10.

Figure 2:
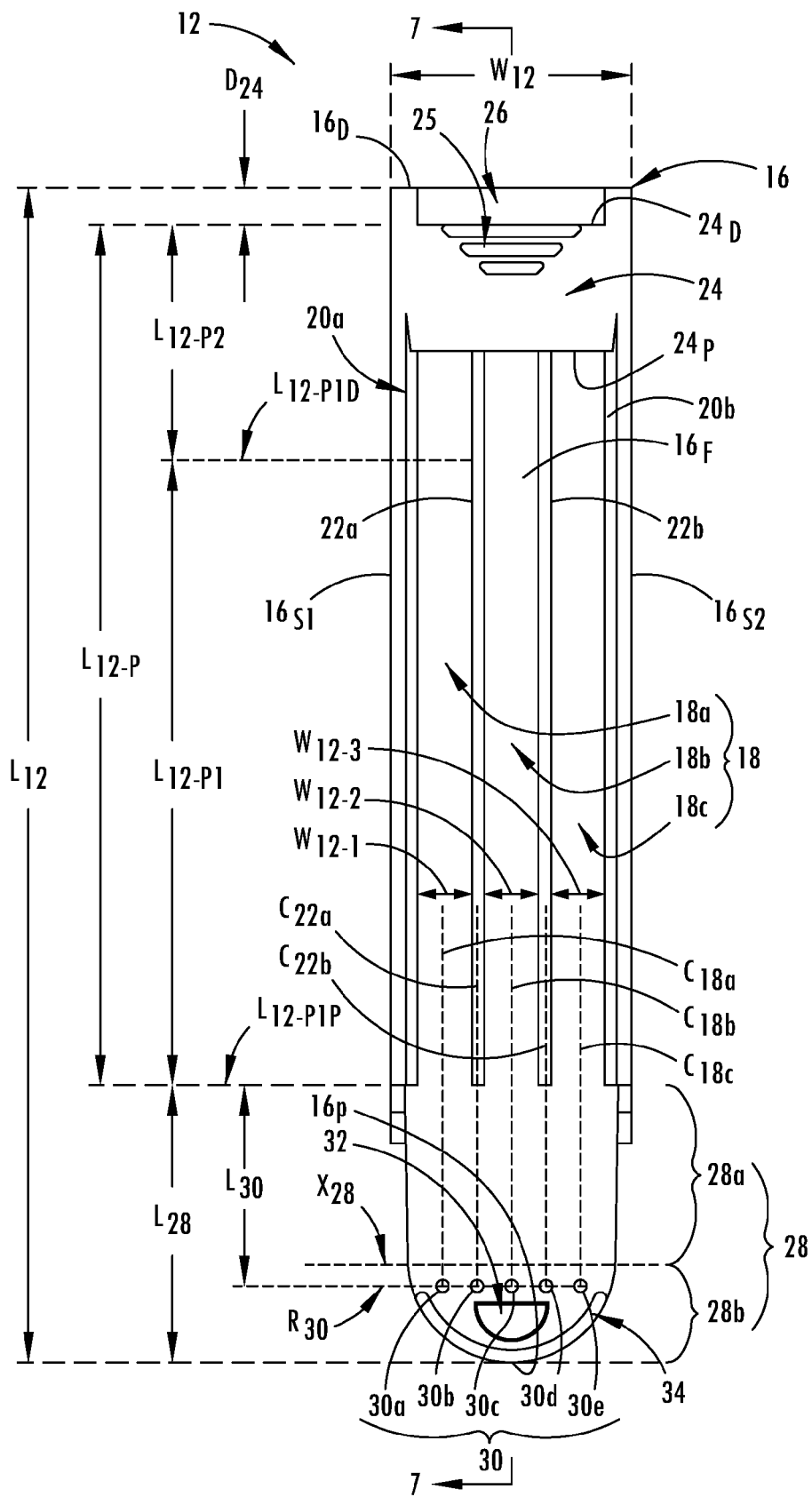
FIG. 2 is a front view of a base portion of the fluid retainer cartridge assembly of FIG. 1A.
Figure 3:
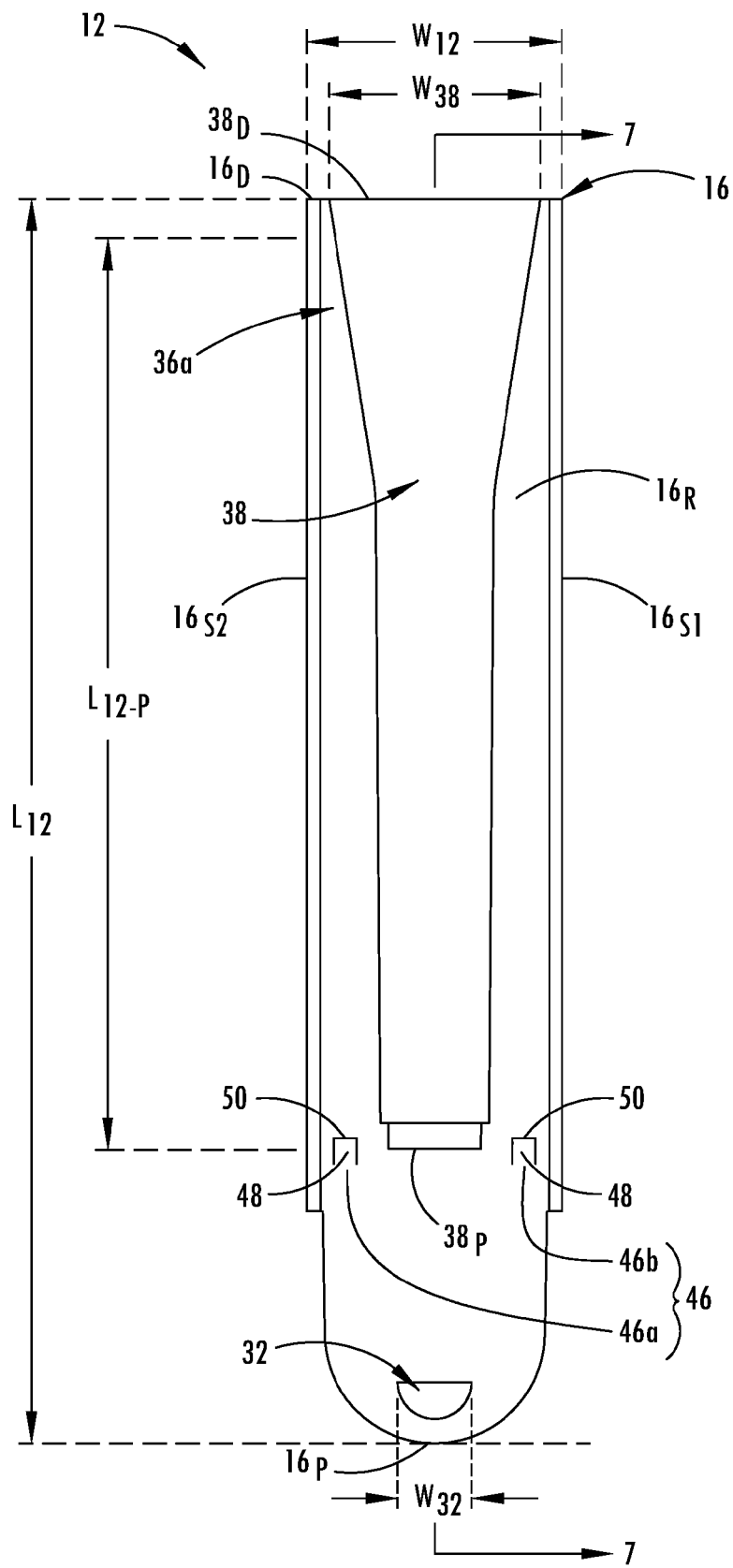
FIG. 3 is a rear view of the base portion of FIG. 2.
Figure 4:
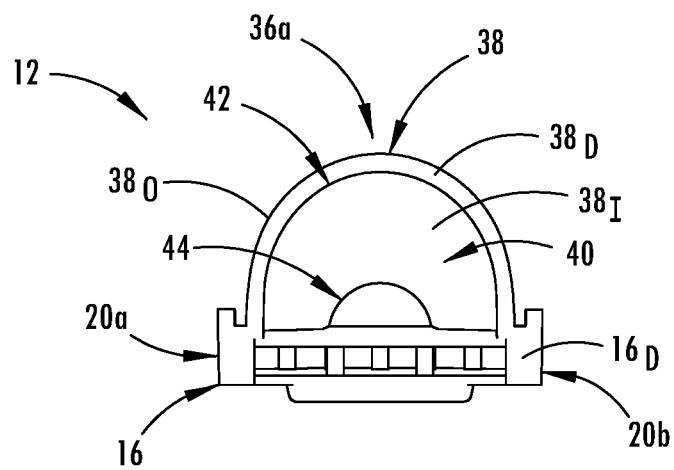
FIG. 4 is a top view of the base portion of FIG. 2.

Referring to FIGS. 2-7, the base portion 12 includes a body 16 that is generally defined by a front surface $16_F$ (see, e.g., FIG. 2), a rear surface $16_R$, (see, e.g., FIG. 3) a distal end surface $16_D$ (see, e.g., FIG. 4), a proximal end surface $16_P$ (see, e.g., FIG. 5), a first side surface $16_{S1}$ (see, e.g., FIG. 6) and a second side surface $16_{S2}$ (see, e.g., FIGS. 3 and 6). As seen in FIGS. 2-3, the base portion 12 is further generally defined by a length $L_{12}$ extending between the distal end surface $16_D$ and the proximal end surface $16_P$. The base portion 12 is yet even further generally defined by a width $W_{12}$ extending between the first side surface $16_{S1}$ and the second side surface $16_{S2}$.

Referring to FIG. 2, the front surface $16_F$ of the body 16 of the base portion 12 generally defines more than one implement-receiving channel 18 (e.g., three implement-receiving channels 18a-18c) extending along a portion $L_{12-P}$ of the length $L_{12}$ of the base portion 12. The more than one implement-receiving channel 18 may be defined by a first sidewall flange 20a, a second sidewall flange 20b, a first rib 22a and a second rib 22b.

The first sidewall flange 20a extends away from the front surface $16_F$ and is arranged proximate the first side surface $16_{S1}$. The second sidewall flange 20b extends away from the front surface $16_F$ and is arranged proximate the second side surface $16_{S2}$. The first rib 22a extends away from the front surface $16_F$ and is arranged proximate the first sidewall flange 20a. The second rib 22b extends away from the front surface $16_F$ and is arranged proximate but spaced-apart from second sidewall flange 20b.

The first sidewall flange 20a is spaced apart from the first rib 22a at a distance equal to a first portion $W_{12-1}$ of the width $W_{12}$ of the base portion 12 for defining a first implement-receiving channel 18a of the more than one implement-receiving channels 18. The first rib 22a is spaced apart from the second rib 18b at a distance equal to a second portion $W_{12-2}$ of the width $W_{12}$ of the base portion 12 for defining a second implement-receiving channel 18b of the more than one implement-receiving channels 18. The second rib 22b is spaced apart from the second sidewall flange 20b at a distance equal to a third portion $W_{12-3}$ of the width $W_{12}$ of the base portion 12 for defining a third implement-receiving channel 18c of the more than one implement-receiving channels 18.

With continued reference to FIG. 2, the front surface $16_F$ of the body 16 of the base portion 12 further defines an implement distal end retainer portion 24. The implement distal end retainer portion 24 extends across the width $W_{12}$ of the base portion 12 and connects the first sidewall flange 20a to the second sidewall flange 20b. Furthermore, the implement distal end retainer portion 24 may be further defined by a distal end $24_D$ and a proximal end $24_P$; the distal end $24_D$ may be arranged at a distance $D_{24}$ away from the distal end surface $16_D$ of the body 16 of the base portion 12 for defining an access port 26 that is sized for permitting insertion of, for example, a user's finger therein for grasping any of the one or more implements I for inserting or removing the one or more implements I from the more than one implement-receiving channels 18. The implement distal end retainer portion 24 may also include a series of friction ribs 25 that may assist a user in grasping the fluid retainer cartridge assembly 10 when inserting or removing the fluid retainer cartridge assembly 10 into/from an implement analyzing device (not shown), such as an optical reader that can monitor, read and analyze the one or more implements I before, during or after being contacted with the fluid F.

With reference to FIGS. 2 and 7, each of the first sidewall flange 20a and the second sidewall flange 20b may extend away from the front surface $16_F$ of the body 16 of the base portion 12 at a substantially constant distance $D_{20}$ (see, e.g., FIG. 7) along the portion $L_{12-P}$ of the length $L_{12}$ of the base portion 12. Each of the first rib 22a and the second rib 22b may extend away from the front surface $16_F$ of the body 16 of the base portion 12 at a substantially constant distance $D_{22-1}$ (see, e.g., FIG. 7) along a first segment $L_{12-P1}$ (see, e.g., FIG. 2) of the portion $L_{12-P}$ of the length $L_{12}$ of the base portion 12. The first segment $L_{12-P1}$ of the portion $L_{12-P}$ of the length $L_{12}$ of the base portion 12 may be bound by a proximal end $L_{12-P1P}$ and a distal end $L_{12-P1D}$. In some examples, each of the first rib 22a and the second rib 22b may extend away from the front surface $16_F$ of the body 16 of the base portion 12 at a progressively-increasing distance $D_{22-2}$ (see, e.g., FIG. 7) from the distal end $L_{12-P1D}$ of the first segment $L_{12-P1}$ of the portion $L_{12-P}$ of the length $L_{12}$ of the base portion 12 along a second segment $L_{12-P2}$ (see, e.g., FIG. 2) of the portion $L_{12-P}$ of the length $L_{12}$ of the base portion 12 toward the proximal end $24_P$ of the implement distal end retainer portion 24.

As seen in FIG. 2, a portion (i.e., a tongue portion 28) of the front surface $16_F$ of the body 16 of the base portion 12 does not include any of the first sidewall flange 20a, the second sidewall flange 20b, the first rib 22a and the second rib 22b. In an example as seen in FIG. 1B, when the one or more implements I are interfaced with the fluid retainer cartridge assembly 10, the one or more implements I may extend out of the more than one implement-receiving channels 18 and over the tongue portion 28.

Referring to FIG. 2, the tongue portion 28 may be defined by a length $L_{28}$ extending between the proximal end $L_{12-P1P}$ of the first segment $L_{12-P1}$ of the portion $L_{12-P}$ of the length $L_{12}$ of the base portion 12 and proximal-most/lower-most portion of the proximal end surface $16_P$ of the body 16 of the base portion 12. In some instances, the proximal end surface $16_P$ may include an arcuate shape that partially defines the tongue portion 28. Furthermore, proximal end surface $16_P$ connects (see, e.g., dashed line $X_{28}$ extending across the tongue portion 28) the first side surface $16_{S1}$ to the second side surface $16_{S2}$. Yet even further, as see in FIG. 2, the first side surface $16_{S1}$ is substantially parallel to the second side surface $16_{S2}$ along the length $L_{28}$ of the tongue portion 28. Therefore, in an example, the tongue portion 28 may be generally defined by: (1) a substantially square or rectangular portion 28a defined in part by the first side surface $16_{S1}$ and the second side surface $16_{S2}$ and (2) a substantially 'half moon' portion 28b defined by the proximal end surface $16_P$, which is demarcated from the substantially square or rectangular portion 28a by the dashed line $X_{28}$.

Although the first sidewall flange 20a, the second sidewall flange 20b, the first rib 22a and the second rib 22b do not extend away from the front surface $16_F$ of the body 16 of the base portion 12 defined by the tongue portion 28, a plurality of projections 30 extend away from the front surface $16_F$ of the body 16 of the base portion 12 defined by the tongue portion 28 at a distance $D_{30}$ (see, e.g., FIG. 7). In some implementations, the plurality of projections 30 may be substantially cylindrical (or they may have another shape for evenly distributing and selectively flowing the fluid F, as described below), and may be linearly-arranged in a row (see, e.g., dashed line $R_{30}$ extending across the 'half moon' portion 28b, which is substantially parallel to the dashed line $X_{28}$). Furthermore, the row $R_{30}$ of the plurality of projections 30 may extend from the 'half moon' portion 28b of the tongue portion and may be arranged at a length $L_{30}$ (see, e.g., FIG. 2) away from the proximal end $L_{12-P1P}$ of the first segment $L_{12-P1}$ of the portion $L_{12-P}$ of the length $L_{12}$ of the base portion 12.

In an example, as seen in FIG. 2, the plurality of projections 30 may be defined by a first projection 30a, a second projection 30b, a third projection 30c, a fourth projection 30d and a fifth projection 30e. In some implementations, the plurality of projections 30 including the first-through-fifth projections 30a-30e may be arranged relative to the first-through-third implement-receiving channels 18a-18c as follows: (1) the first projection 30a may be aligned with a center (see, e.g., dashed line $C_{18a}$) of the first portion $W_{12-1}$ of the width $W_{12}$ defining the first implement-receiving channel 18a, (2) the second projection 30b may be aligned with a center (see, e.g., dashed line $C_{22a}$) of the first rib 22a that partially defines each of the first and second implement-receiving channels 18a, 18b, (3) the third projection 30c may be aligned with a center (see, e.g., dashed line $C_{18b}$) of the second portion $W_{12-2}$ of the width $W_{12}$ defining the second implement-receiving channel 18b, (4) the fourth projection 30d may be aligned with a center (see, e.g., dashed line $C_{22b}$) of the second rib 22b that partially defines each of the second and third implement-receiving channels 18b, 18c and (5) the fifth projection 30e may be aligned with a center (see, e.g., dashed line $C_{18c}$) of the third portion $W_{12-3}$ of the width $W_{12}$ defining the third implement-receiving channel 18c.

In an example, the tongue portion 28 may further define a fluid-flow passage 32 extending through a thickness $T_{16}$ (see, e.g., FIG. 7) of the body 16 of the base portion 12. The thickness $T_{16}$ of the body 16 of the base portion 12 (as defined by the tongue portion 28) is bound by the front surface $16_F$ of the body 16 of the base portion 12 and the rear surface $16_R$ of the body 16 of the base portion 12. Furthermore, as seen in FIGS. 2-3, the fluid-flow passage 32 may be defined by the substantially 'half moon' portion 28b of the tongue portion 28. In some instances, the fluid-flow passage 32 may include a smaller, but substantially proportional 'half-moon' geometry compared to the 'half moon' portion 28b of the tongue portion 28 and includes a maximum width $W_{32}$ (see, e.g., FIG. 3) that extends between an laterally-outward-most portion of each of the second projection 30b and the fourth projection 30d.

In yet another example, the tongue portion 28 may further define a fluid-flow guide rib 34. The fluid-flow guide rib 34 may extend away from the front surface $16_F$ of the body 16 of the base portion 12 defined by the substantially 'half moon' portion 28b of the tongue portion 28 at a distance $D_{34}$ (see, e.g., FIG. 7). Furthermore, as seen in FIG. 2, the fluid-flow guide rib 34 may include an arcuate shape and extend away from the front surface $16_F$ of the body 16 of the base portion 12 defined by the substantially 'half moon' portion 28b of the tongue portion 28 proximate the proximal end surface $16_P$ of the body 16 of the base portion 12.

Referring to FIG. 1A, the fluid retainer cartridge assembly 10 may further define a fluid guide portion 36. In an example, the fluid guide portion 36 may be defined by a funnel portion 36a formed by the base portion 12 and a fluid conduit portion 36b formed by the cap portion 14.

Referring to FIGS. 3-7, the funnel portion 36a is generally defined by a funnel body 38 that extends away from the rear surface $16_R$ of the base portion 12. As seen in FIG. 3, the funnel body 38 may be defined by a distal surface $38_D$, which may be defined, in part, by the distal surface $16_D$ of the body 16 of the base portion 12, and a proximal surface $38_P$. With continued reference to FIG. 3, the funnel body 38 may include a length defined approximately by the portion $L_{12-P}$ of the length $L_{12}$ of the base portion 12. The funnel body 38 may be defined by a width $W_{38}$ that narrows for at least a portion of the length $L_{12-P}$ of the funnel body 38 as the funnel body 38 extends from the distal surface $38_D$ to the proximal surface $38_P$.

Referring to FIG. 7, the funnel body 38 is generally defined by an inner surface $38_I$ and an outer surface $38_O$. The inner surface $38_I$ is arranged in an opposing relationship with respect to the rear surface $16_R$ of the body 16 of the base portion 12 and forms a fluid-flow passage 40 extending through the funnel body 38. Access to the fluid-flow passage 40 is formed by an upstream opening 42 (see, e.g., FIGS. 4 and 7) that permits entry of the fluid F into the funnel body 38 and a downstream opening 44 (see, e.g., FIGS. 4 and 5) that permits the fluid F to exit the funnel body 38.

The fluid-flow passage 40 may be defined by an arcuate channel having a radius $R_{40}$ or radial geometric component. Furthermore, as seen in FIG. 7, the radius $R_{40}$ may be greater near the distal surface $38_D$ of the funnel body 38 such that the upstream opening 42 forms a larger opening or mouth portion of the fluid-flow passage 40 of the funnel body 38 than that of the downstream opening 44, which may form a relatively smaller opening or throat portion of the fluid-flow passage 40 of the funnel body 38.

Figure 5:
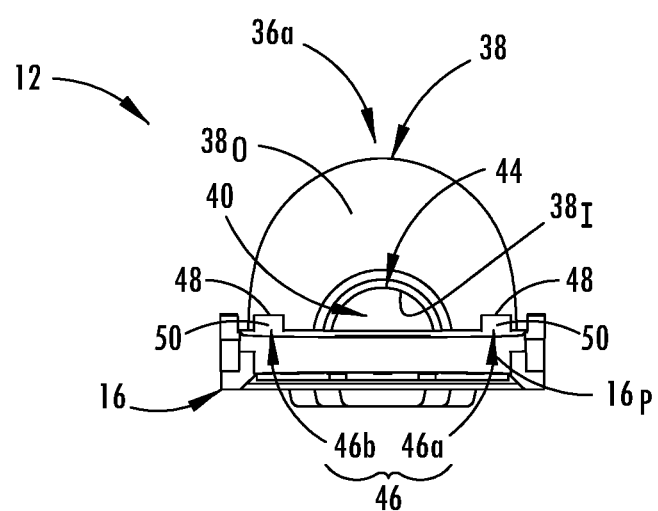
FIG. 5 is a bottom view of the base portion of FIG. 2.
Figure 15A:
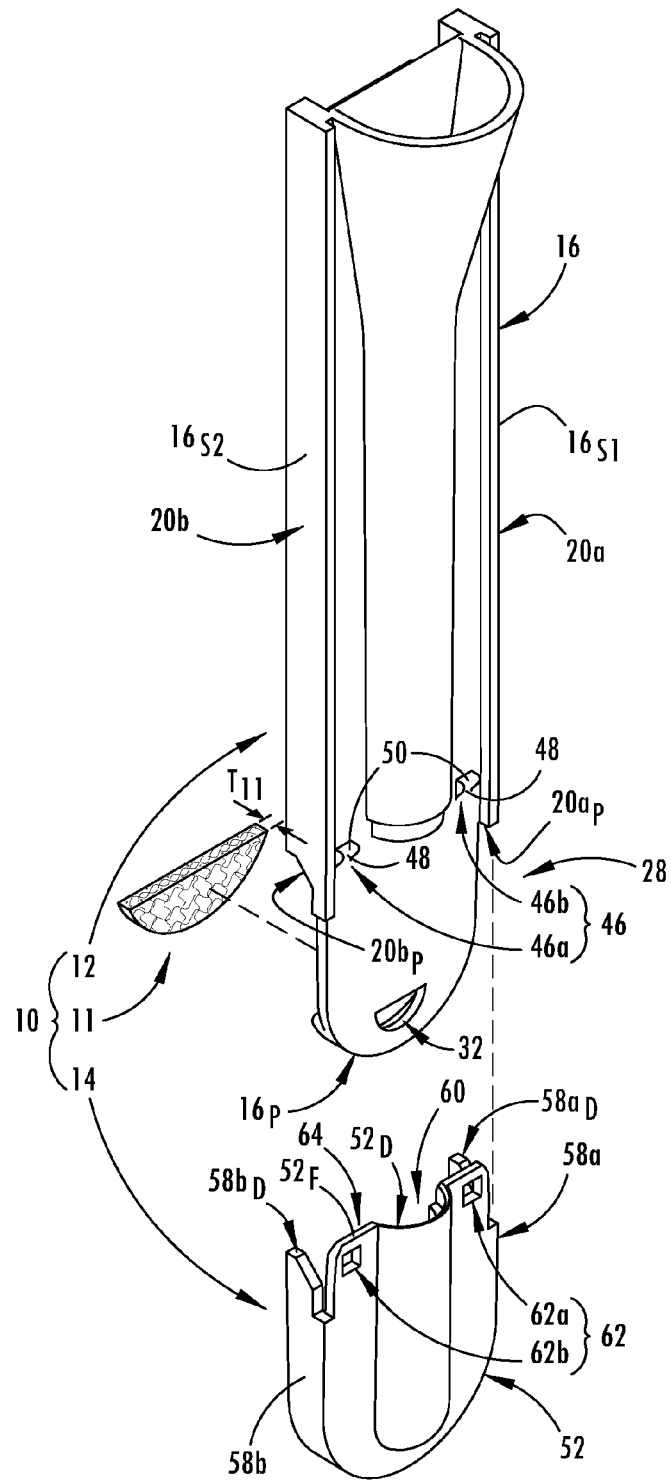
FIG. 15A is a rear exploded view of the fluid retainer cartridge assembly of FIG. 1A.

Referring to FIGS. 3 and 5, the rear surface $16_R$ of the base portion 12 may also define a cap-retainer portion 46. The cap-retainer portion 46 may defined by a pair of protrusions including a first protrusion 46a and a second protrusion 46b that extend away from the rear surface $16_R$ of the base portion 12. The first protrusion 46a and the second protrusion 46b may be respectively arranged near opposite sides of the funnel body 38 and near the proximal surface $38_P$ of the funnel body 38. Each of the first protrusion 46a and the second protrusion 46b may be defined by a ramp surface 48 and latch surface 50 (FIG. 15A).

Referring to FIGS. 8-13, the cap portion 14 of the fluid retainer cartridge assembly 10 includes a body 52 and a tongue-receiving housing 54 connected to the body 52. The body 52 is generally defined by a front surface $52_F$, a rear surface $52_R$, a distal end surface $52_D$, a proximal end surface $52_P$, a first side surface $52_{S1}$ and a second side surface $52_{S2}$. The cap portion 14 is further generally defined by a length $L_{14}$ (see, e.g., FIGS. 8-9 and 12-13) extending between the distal end surface $52_D$ and the proximal end surface $52_P$. The cap portion 14 is yet even further generally defined by a width $W_{14}$ (see, e.g., FIGS. 8-11) extending between the first side surface $52_{S1}$ and the second side surface $52_{S2}$.

Figure 8:
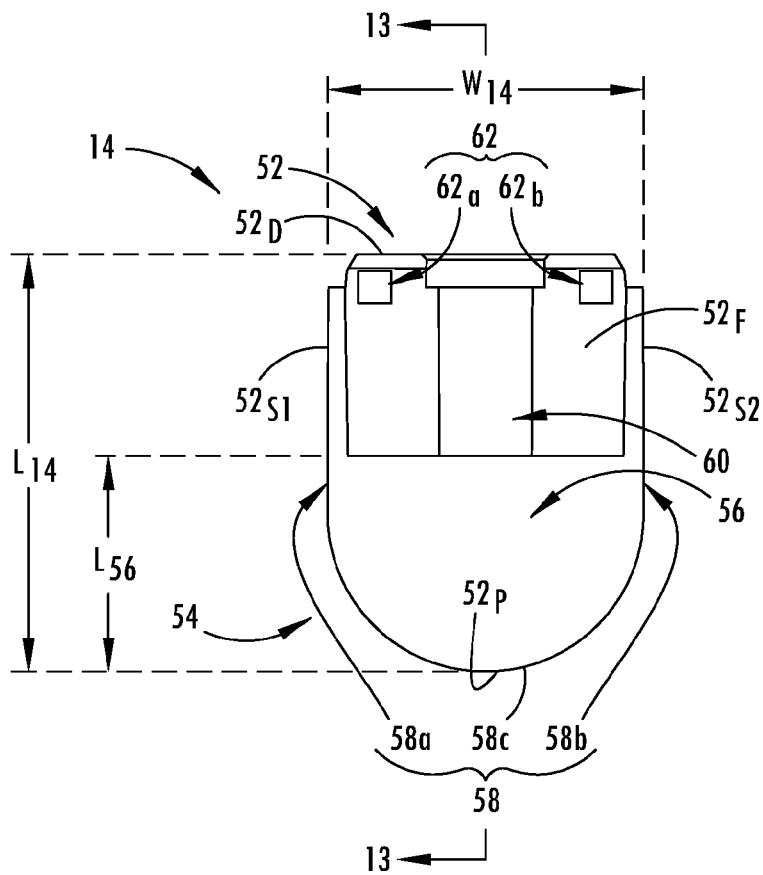
FIG. 8 is a front view of a cap portion of the fluid retainer cartridge assembly of FIG. 1A.

As seen in FIG. 8, the tongue-receiving housing 54 may be defined by an implement proximal end retainer portion 56 and a flange portion 58 defined by a first sidewall flange segment 58a, a second sidewall flange segment 58b and an arcuate flange segment 58c. The implement proximal end retainer portion 56 extends across a width $W_{14}$ of the base portion 14 and is connected to each of the first sidewall flange segment 58a, the second sidewall flange segment 58b and the arcuate flange segment 58c. The implement proximal end retainer portion 56 extends away from the arcuate flange segment 58c toward the distal end surface $52_D$ of the body 52 at a length $L_{56}$; the length $L_{56}$ of the implement proximal end retainer portion 56 may be equal to approximately half of the length $L_{14}$ of the cap portion 14.

With continued reference to FIG. 8, the first sidewall flange segment 58a extends away from the front surface $52_F$ and is arranged proximate the first side surface $52_{S1}$. The second sidewall flange segment 58b extends away from the front surface $52_F$ and is arranged proximate the second side surface $52_{S2}$. The arcuate flange segment 58c extends away from the front surface $52_F$ and is arranged proximate the proximal surface $52_P$.

Figure 12:
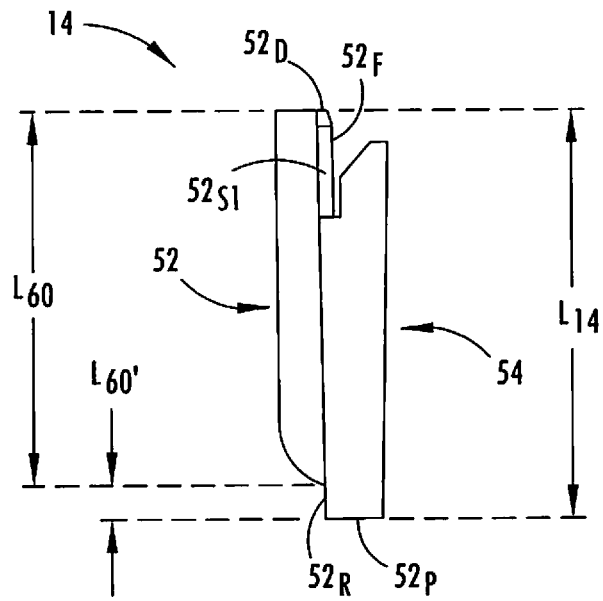
FIG. 12 is a side view of the cap portion of FIG. 6.
Figure 13:
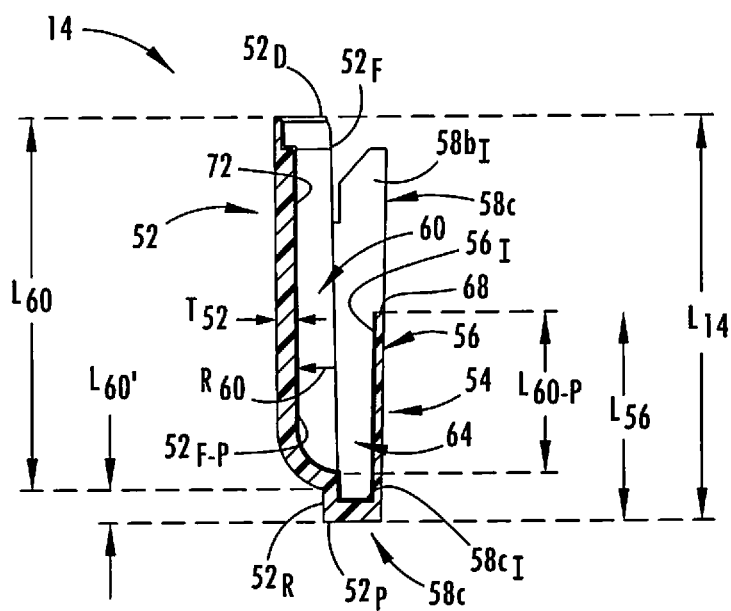
FIG. 13 is a cross-sectional view of the base portion according to line 13-13 of FIG. 8.

Referring to FIG. 13, the body 52 of the cap portion 14 may include a substantially constant thickness $T_{52}$. As seen in FIGS. 8-13, the body 52 defined by the substantially constant thickness $T_{52}$ is not substantially planar, and, as a result, the body 52 may form an arcuate-shaped channel 60 (see, e.g., FIGS. 8, 10, 13) defined by a radius $R_{60}$ (see, e.g., FIGS. 10, 13) or radial geometric component extending into the front surface $52_F$ of the body 52, which results in the rear surface $52_R$ of the body 52 defining an arcuate projection.

Figure 9:
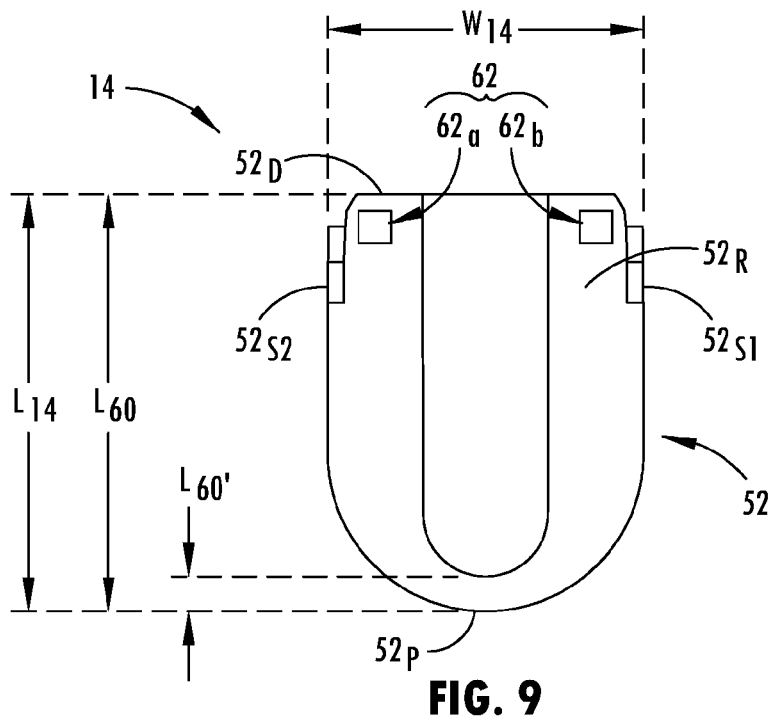
FIG. 9 is a rear view of the cap portion of FIG. 6.

Referring to FIGS. 9 and 12-13, the arcuate-shaped channel 60 may be defined by a length $L_{60}$ that extends along a portion of the length $L_{14}$ of the cap portion 14 from the distal end surface $52_D$ of the body 52 toward the proximal end surface $52_P$ of the body 52. Furthermore, a remainder of the length $L_{14}$ of the cap portion 14 where the arcuate-shaped channel 60 is not formed is shown generally at $L_{60}'$. Yet even further, as seen in FIG. 13, a portion $L_{60-P}$ of the length $L_{60}$ of the arcuate-shaped channel 60 extends along a portion of the length $L_{56}$ of the implement proximal end retainer portion 56.

Referring to FIGS. 8-9, a pair of protrusion-receiving passages 62 extend through the thickness $T_{52}$ of the body 52. The pair of protrusion-receiving passages 62 may defined by a first protrusion-receiving passage 62a and a second protrusion-receiving passage 62b. The first protrusion-receiving passage 62a and the second protrusion-receiving passage 62b may be respectively arranged near opposite sides of the arcuate-shaped channel 60.

Figure 10:
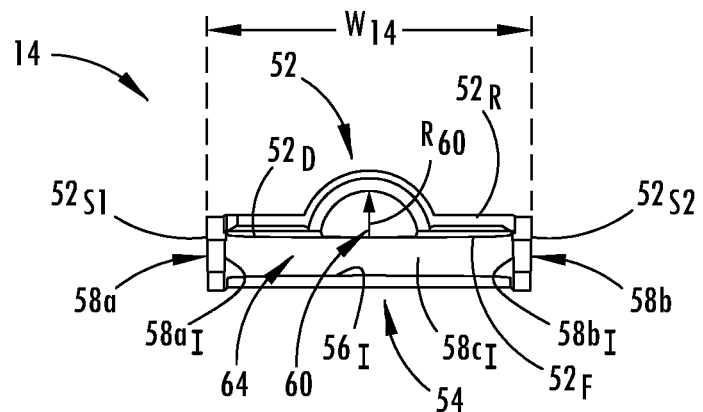
FIG. 10 is a top view of the cap portion of FIG. 6.
Figure 11:
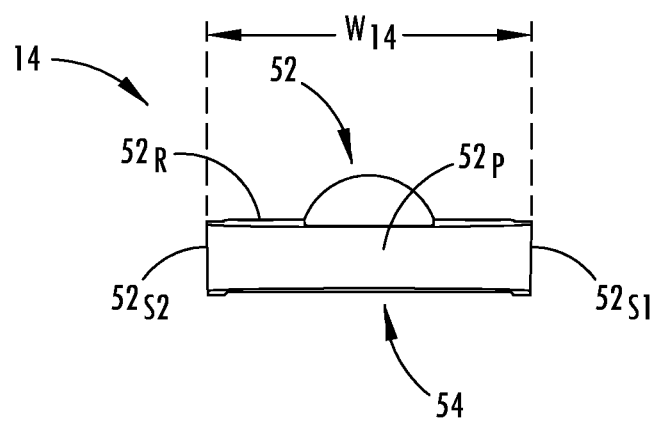
FIG. 11 is a bottom view of the cap portion of FIG. 6.

As seen in FIGS. 10 and 13, the cap portion 14 forms a fluid-receiving void 64. The fluid-receiving void 64 is generally defined by an inner surface $56_I$ of the implement proximal end retainer portion 56, an inner surface $58c_I$ of the arcuate flange segment 58c, a portion of an inner surface $58a_I$, $58b_I$ of each of the first sidewall flange segment 58a and the second sidewall flange segment 58b that extends along the length $L_{56}$ of the implement proximal end retainer portion 56, and a portion $52_{F-P}$ of the front surface $52_F$ that extends along the length $L_{56}$ of the implement proximal end retainer portion 56.

Referring to FIGS. 14A-15B, a method for forming the fluid retainer cartridge assembly 10 is described. In a first optional step, as seen at FIGS. 14A and 15A, the fluid filter 11 may be inserted on the front surface $16_F$ in the substantially half-moon portion 28b of the tongue portion 28 and between projections 30 and fluid-flow guide rib 34 (i.e., as described herein-below, the fluid filter 11 may be inserted in a downstream fluid-receiving void 64b). The fluid filter 11 may be sized and configured to be arranged in this location in a friction-fit relationship. Furthermore, the fluid filter 11 may be sized to have a thickness $T_{11}$ that is similar to the height of the projections 30 and/or fluid-flow guide rib 34 above the front surface $16_F$, e.g., the distance $D_{30}$ less the thickness $T_{16}$, or the distance $D_{34}$ less the thickness $T_{16}$ (FIG. 7). Although an implementation of the fluid retainer cartridge assembly 10 may include the fluid filter 11, the fluid filter 11 may be omitted from the design of the fluid retainer cartridge assembly 10.

Although an implementation of the fluid retainer cartridge assembly 10 may include one fluid filter 11 as described above, the fluid retainer cartridge assembly 10 may include one or more second filters. In an example, a second filter or pre-filter 11a may be connected to the base portion 12. Because the pre-filter 11a is located upstream of the filter 11, the pre-filter 11a may be referred to as an upstream filter and the filter 11 may be referred to as a downstream filter. In an implementation, the pre-filter 11a may be disposed within the fluid-flow passage 40 extending through the funnel body 38 proximate or near the distal surface $38_D$ of the funnel body 38. Therefore, the pre-filter 11a may filter a 'dirty' fluid F prior to the fluid F being passed through the fluid filter 11.

As seen in FIGS. 14A and 15A, the distal end surface $52_D$ of the body 52 of the cap portion 14 is axially aligned with the proximal end surface $16_P$ of the body 16 of the base portion 12. Furthermore, as seen in FIGS. 14A and 15A, the tongue portion 28 of the base portion 12 is axially aligned with the fluid-receiving void 64 formed by the tongue-receiving housing 54 of the cap portion 14. When the base portion 12 and the cap portion 14 are axially aligned as described above, the fluid-flow passage 40 extending through the funnel body 38 of the base portion 12 is axially aligned with the arcuate-shaped channel 60 formed by the body 52 of the cap portion 14.

With reference to FIG. 14A, the first side surface $16_{S1}$ defining a proximal end $20a_P$ of the first sidewall flange 20a of the base portion 12 may define a recess that corresponds to a projection defined by a distal end $58a_D$ of the first sidewall flange segment 58a of the cap portion 14. Similarly, as seen in FIG. 15A, the second side surface $16_{S2}$ defining a proximal end $20b_P$ of the second sidewall flange 20b of the base portion 12 may define a recess that corresponds to a projection defined by a distal end $58b_D$ of the second sidewall flange segment 58b of the cap portion 14.

Figure 15B:
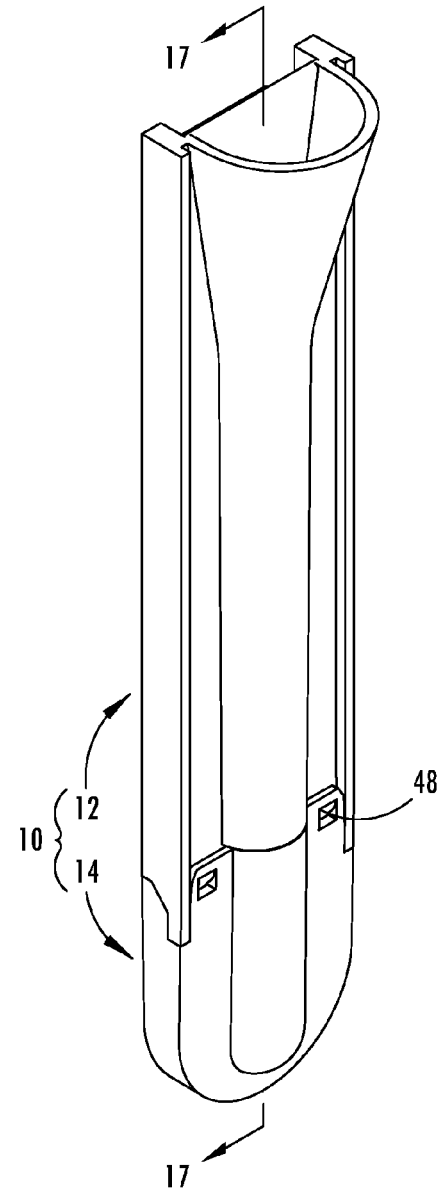
FIG. 15B is a rear assembled view of the fluid retainer cartridge assembly of FIG. 15A.

Furthermore, as seen in FIG. 15A, when the base portion 12 and cap portion 14 are axially aligned as described above, the cap-retainer portion 46 (of the base portion 12) defined by the first protrusion 46a and the second protrusion 46b are axially aligned with the pair of protrusion-receiving passages 62 (of the cap portion 14) defined by the first protrusion-receiving passage 62a and the second protrusion-receiving passage 62b. As the tongue portion 28 of the base portion 12 is inserted into the fluid-receiving void 64 of the cap portion 14, the ramp surface 48 of each of the first protrusion 46a and the second protrusion 46b contacts and rides adjacent the front surface $52_F$ (proximate the distal end surface $52_D$) of the body 52 for respectively advancing each of the first protrusion 46a and the second protrusion 46b into the first protrusion-receiving passage 62a and the second protrusion-receiving passage 62b. Just after the ramp surface 48 of each of the first protrusion 46a and the second protrusion 46b has been respectively aligned with the first protrusion-receiving passage 62a and the second protrusion-receiving passage 62b, the body 52 (proximate the distal end surface $52_D$) of the cap portion 14 flexes over the latch surface 50 of each of the first protrusion 46a and the second protrusion 46b for removably-attaching the cap portion 14 to the base portion 12 as seen in FIGS. 14B and 15B.

Figure 16:
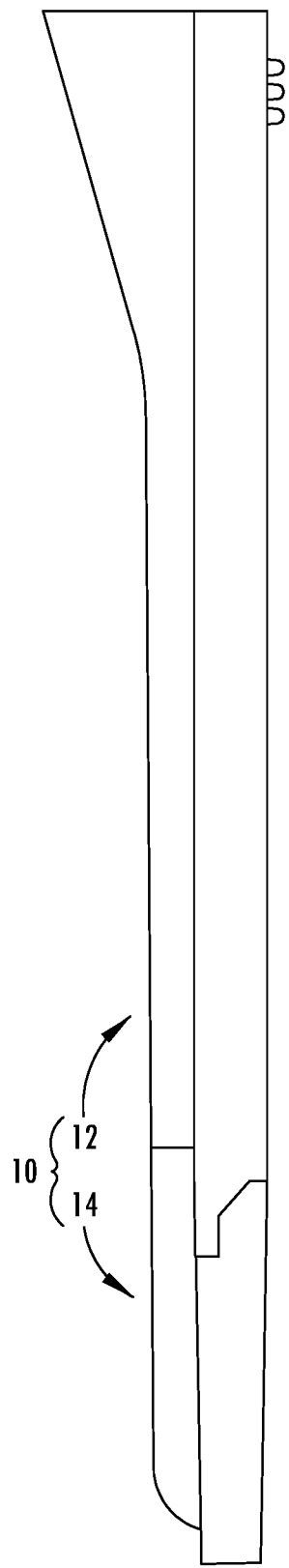
FIG. 16 is a side view of the fluid retainer cartridge assembly of FIG. 14B or FIG. 15B.
Figure 17:
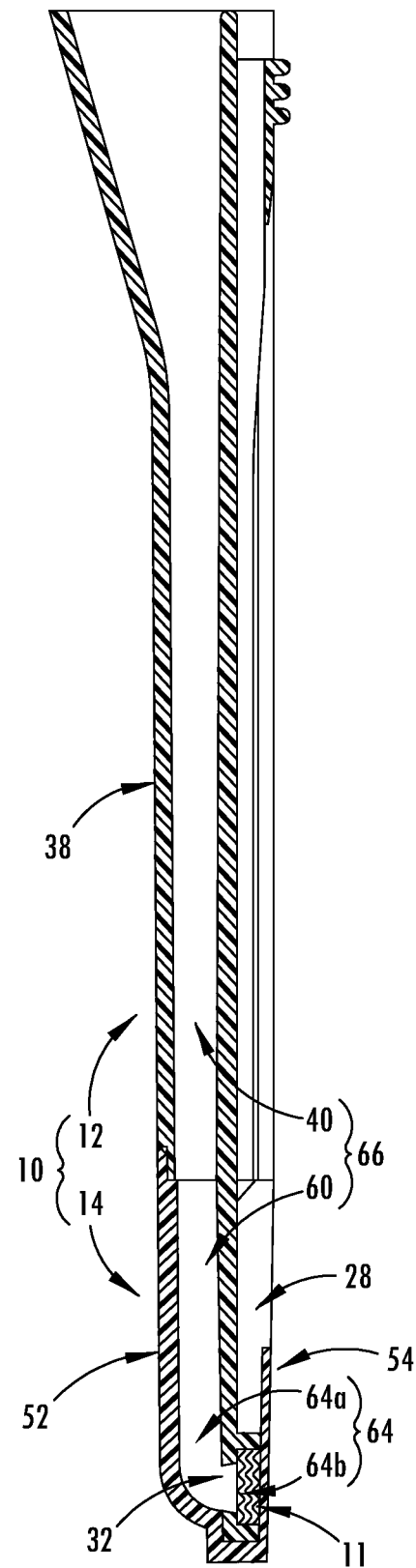
FIG. 17 is a cross-sectional view of the fluid retainer cartridge assembly according to line 17-17 of FIG. 14B or FIG. 15B.

Referring to FIGS. 16-17, the base portion 12 and the cap portion 14 are shown in a removably-attached configuration after the first protrusion 46a and the second protrusion 46b are arranged within the first protrusion-receiving passage 62a and the second protrusion-receiving passage 62b. With reference to FIG. 17, the fluid-flow passage 40 extending through the funnel body 38 of the base portion 12 is fluidly-connected to the arcuate-shaped channel 60 formed by the body 52 of the cap portion 14 for forming an axial fluid conduit 66 of the fluid retainer cartridge assembly 10. Furthermore, as seen in FIG. 17, after the first protrusion 46a and the second protrusion 46b are arranged within the first protrusion-receiving passage 62a and the second protrusion-receiving passage 62b for removably-attaching the base portion 12 to the cap portion 14, the tongue portion 28 of the base portion 12 is fully axially disposed within the fluid-receiving void 64 formed by the tongue-receiving housing 54 of the cap portion 14 such that the tongue portion 28 fluidly-divides the fluid-receiving void 64 into an upstream fluid-receiving void 64a and the downstream fluid-receiving void 64b. The upstream fluid-receiving void 64a is in fluid communication with the downstream fluid-receiving void 64b by way of the fluid-flow passage 32 of the tongue portion 28.

If the fluid filter 11 is disposed within the downstream fluid-receiving void 64b, any fluid F that passes from the upstream fluid-receiving void 64a to the downstream fluid-receiving void 64b by way of the fluid-flow passage 32 will be filtered by the fluid filter 11; in such an implementation, the upstream fluid-receiving void 64a may be referred to as an unfiltered reservoir portion of the fluid-receiving void 64 and the downstream fluid-receiving void 64b may be referred to as a filtered reservoir portion of the fluid-receiving void 64. However, if the fluid filter 11 is not disposed within the downstream fluid-receiving void 64b, any fluid F that enters the downstream fluid-receiving void 64b from the upstream fluid-receiving void 64a by way of the fluid-flow passage 32 of the tongue portion 28 is not filtered.

Figure 18:
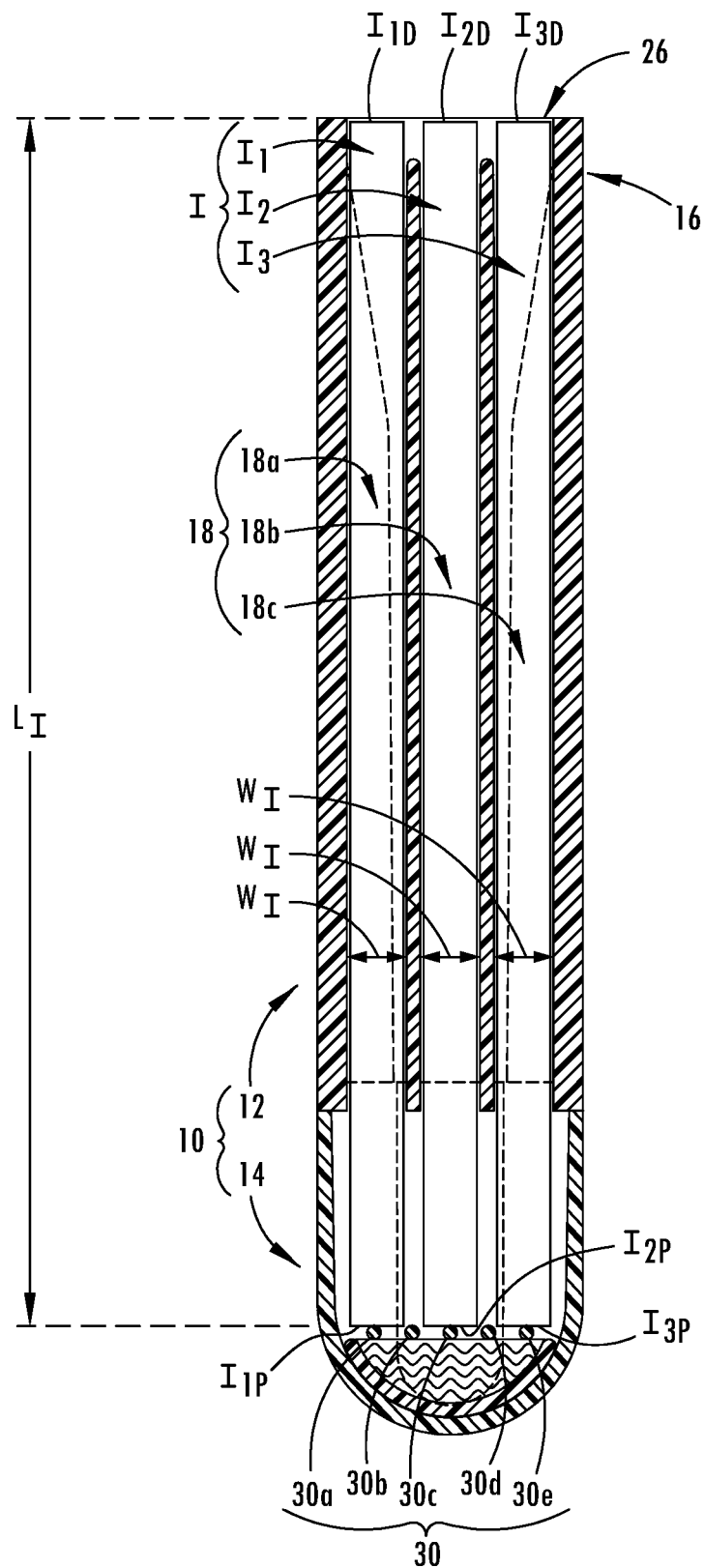
FIG. 18 is a cross-sectional view of the fluid retainer cartridge assembly according to line 18-18 of FIG. 1B.

Referring to FIGS. 1A-1B and 18, a plurality of implements I (e.g., a plurality of test strip assays) are interfaced with the fluid retainer cartridge assembly 10. The plurality of test strip assays I includes three test strip assays, being: a first test strip assay $I_1$, a second test strip assay $I_2$ and a third test strip assay $I_3$.

As seen in FIGS. 1A and 18, the plurality of test strip assays I are disposed into the fluid retainer cartridge assembly 10 by way of the access port 26 formed by the body 16 of the base portion 12 such that the plurality of test strip assays I are arranged within the plurality of implement-receiving channels 18. In an example, the plurality of test strip assays I may be arranged within the plurality of implement-receiving channels 18 as follows: (1) the first test strip assay $I_1$ is arranged within the first implement-receiving channel 18a, (2) the second test strip assay $I_2$ is arranged within the second implement-receiving channel 18b and (3) the third test strip assay $I_3$ is arranged within the third implement-receiving channel 18c.

Referring to FIG. 18, insertion of the plurality of test strip assays I into the fluid retainer cartridge assembly 10 ceases once a proximal end $I_{1P}$, $I_{2P}$, $I_{3P}$ of each test strip assay $I_1$, $I_2$, $I_3$ engages a corresponding projection 30a, 30c, 30e of the plurality of projections 30. For example, as seen in FIG. 18: (1) the proximal end lip of the first test strip assay $I_1$ engages the first projection 30a that is aligned with the center $C_{18a}$ (see, e.g., FIG. 2) of the first portion $W_{12-1}$ of the width $W_{12}$ of the base portion 12 that defines the first implement-receiving channel 18a, (2) the proximal end $I_{2P}$ of the second test strip assay 12 engages the third projection 30c that is aligned with the center $C_{18b}$ (see, e.g., FIG. 2) of the second portion $W_{12-2}$ of the width $W_{12}$ of the base portion 12 that defines the second implement-receiving channel 18b and (3) the proximal end $I_{3P}$ of the third test strip assay 13 engages the fifth projection 30e that is aligned with the center $C_{18c}$ (see, e.g., FIG. 2) of the third portion $W_{12-3}$ of the width $W_{12}$ of the base portion 12 that defines the third implement-receiving channel 18c.

As seen in FIG. 18, each test strip assay $I_1$, $I_2$, $I_3$ of the plurality of test strip assays I includes a width $W_I$ and a length $L_I$. The width $W_I$ of each test strip assay $I_1$, $I_2$, $I_3$ is respectively approximately equal to the width portion $W_{12-1}$, $W_{12-2}$, $W_{12-3}$ (see, e.g., FIG. 2) of the width $W_{12}$ of the base portion 12 that defines each implement-receiving channel 18a, 18b, 18c of the plurality of implement-receiving channels 18. With reference to FIGS. 1B and 18, the length $L_I$ of each test strip assay $I_1$, $I_2$, $I_3$ is selectively sized such that when the proximal end $I_{1P}$, $I_{2P}$, $I_{3P}$ of each test strip assay $I_1$, $I_2$, $I_3$ engages a corresponding projection 30a, 30c, 30e of the plurality of projections 30, a distal end $I_{1D}$, $I_{2D}$, $I_{3D}$ of each test strip assay $I_1$, $I_2$, $I_3$ is accessible at the access port 26 for permitting, for example, insertion of a user's finger therein for grasping any of the first, second or third test strip assays $I_1$, $I_2$, $I_3$ for inserting or removing any of the first, second or third test strip assays $I_1$, $I_2$, $I_3$ from any of the first, second or third implement-receiving channels 18a, 18b, 18c.

Figure 19:
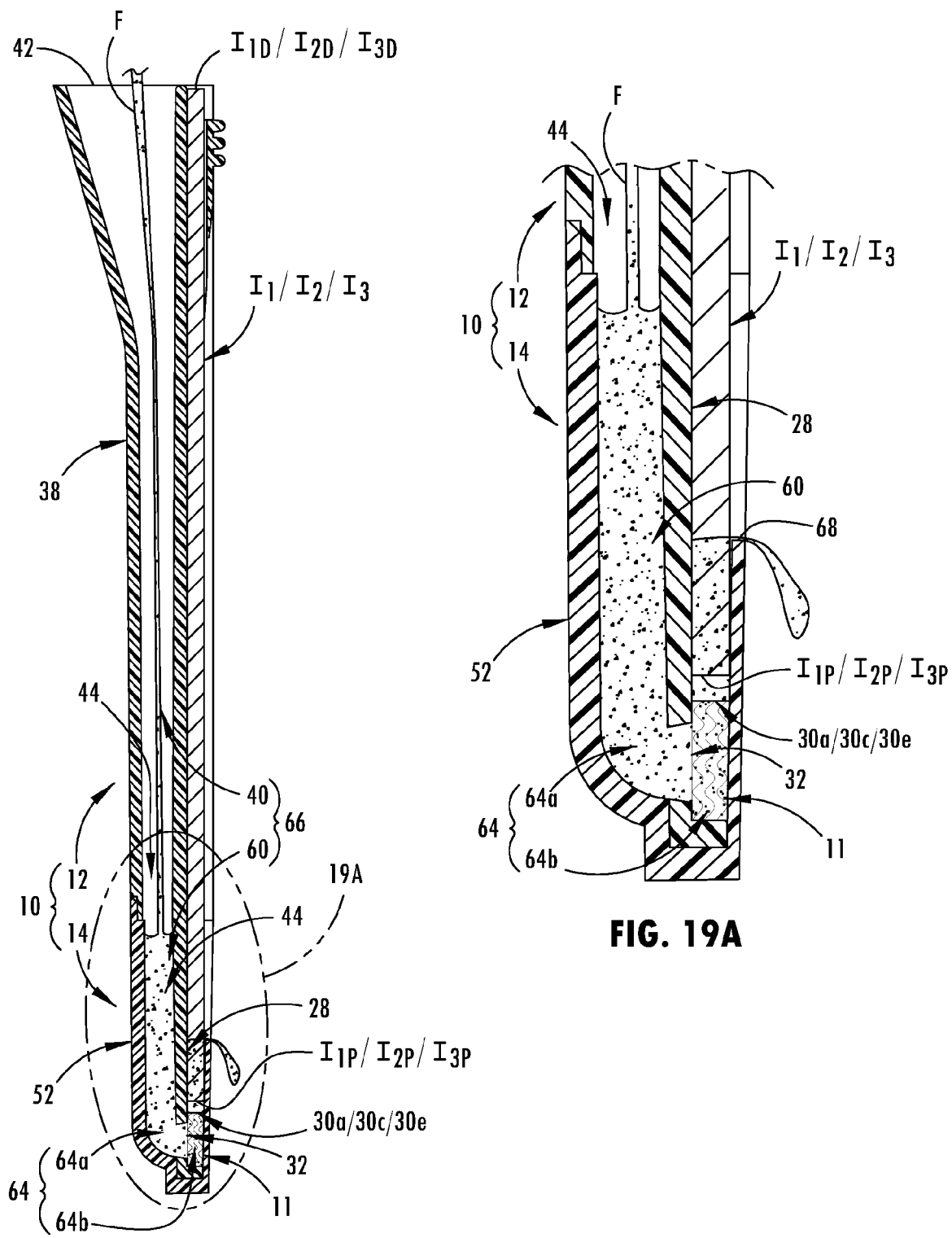
FIG. 19 is a cross-sectional view of the fluid retainer cartridge assembly according to line 19-19 of FIG. 1B.

Referring to FIGS. 1B and 19-21A, fluid F is poured into the fluid retainer cartridge assembly 10. As seen in FIGS. 1B, 19 and 19A, the fluid F initially enters the axial fluid conduit 66 of the fluid retainer cartridge assembly 10 by way of the upstream opening 42 of the funnel body 38 formed by the base portion 12. The fluid F passes through the fluid-flow passage 40 of the funnel body 38 of the base portion 12 and subsequently exits the fluid-flow passage 40 of the funnel body 38 of the base portion 12 at the downstream opening 44. The fluid F then enters the arcuate-shaped channel 60 formed by the body 52 of the cap portion 14 that is in fluid communication with the fluid-flow passage 40 of the funnel body 38 of the base portion 12 at the downstream opening 44 such that the fluid F ultimately arrives at the upstream fluid-receiving void 64a of the fluid-receiving void 64. In an example, as seen in FIG. 19A, an amount of the fluid F that exceeds the volume of the fluid-receiving void 64, exits the fluid retainer cartridge assembly 10 by spilling over a fluid overflow edge 68, which may be a portion of the distal end surface $52_D$, formed by the front surface $52_F$ of the body 52 of the cap portion 14.

Figure 20:
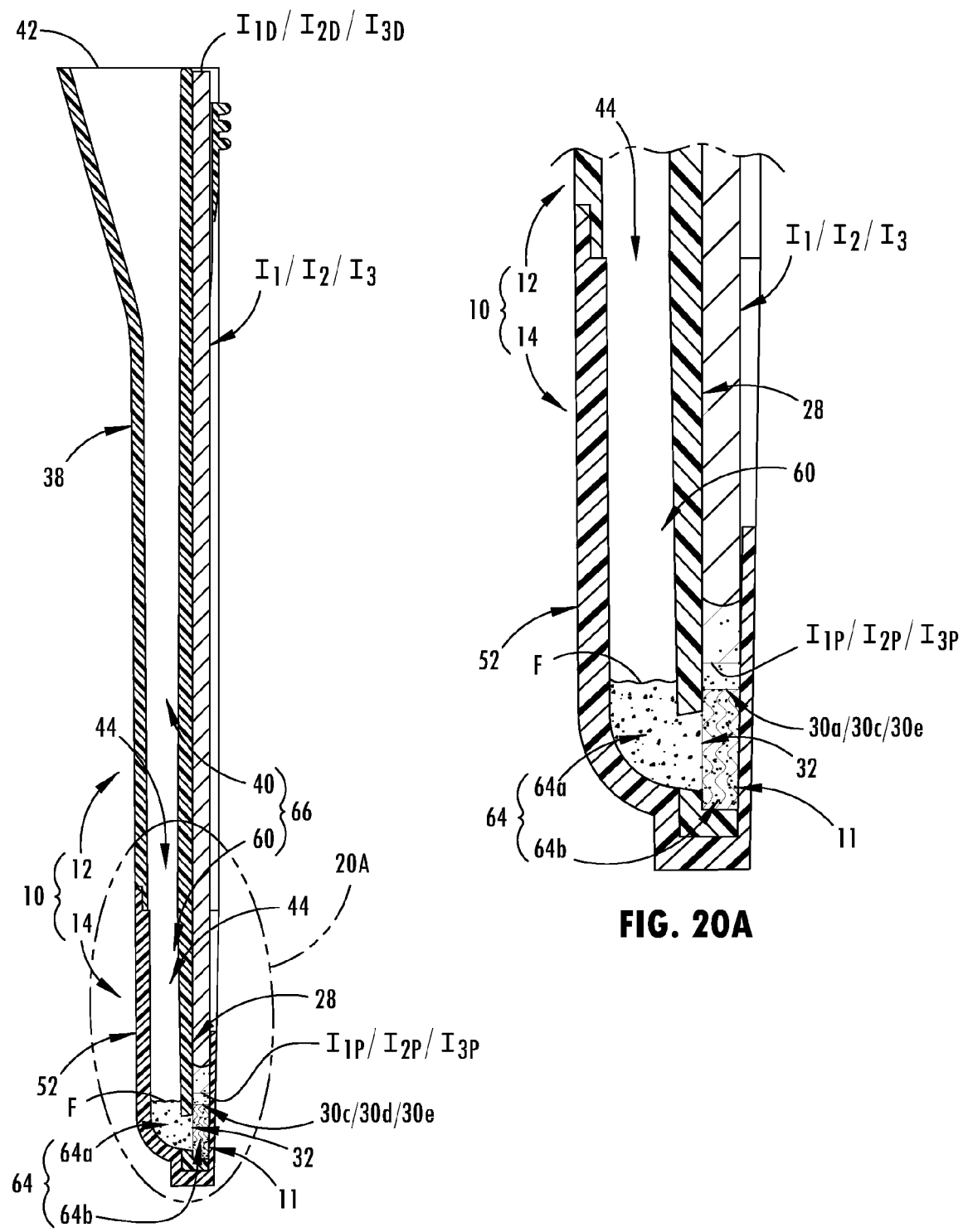
FIG. 20 is another cross-sectional view of the fluid retainer cartridge assembly according to FIG. 19.

As seen in FIGS. 20 and 20A, the fluid F may radially pass from the upstream fluid-receiving void 64a of the fluid-receiving void 64 and into the downstream fluid-receiving void 64b of the fluid-receiving void 64. As seen in FIGS. 20 and 20A, the fluid filter 11 is shown optionally inserted into the downstream fluid-receiving void 64b for filtering the fluid F as the fluid F migrates radially through the fluid filter 11 from the upstream fluid-receiving void 64a into the downstream fluid-receiving void 64b.

Figure 21:
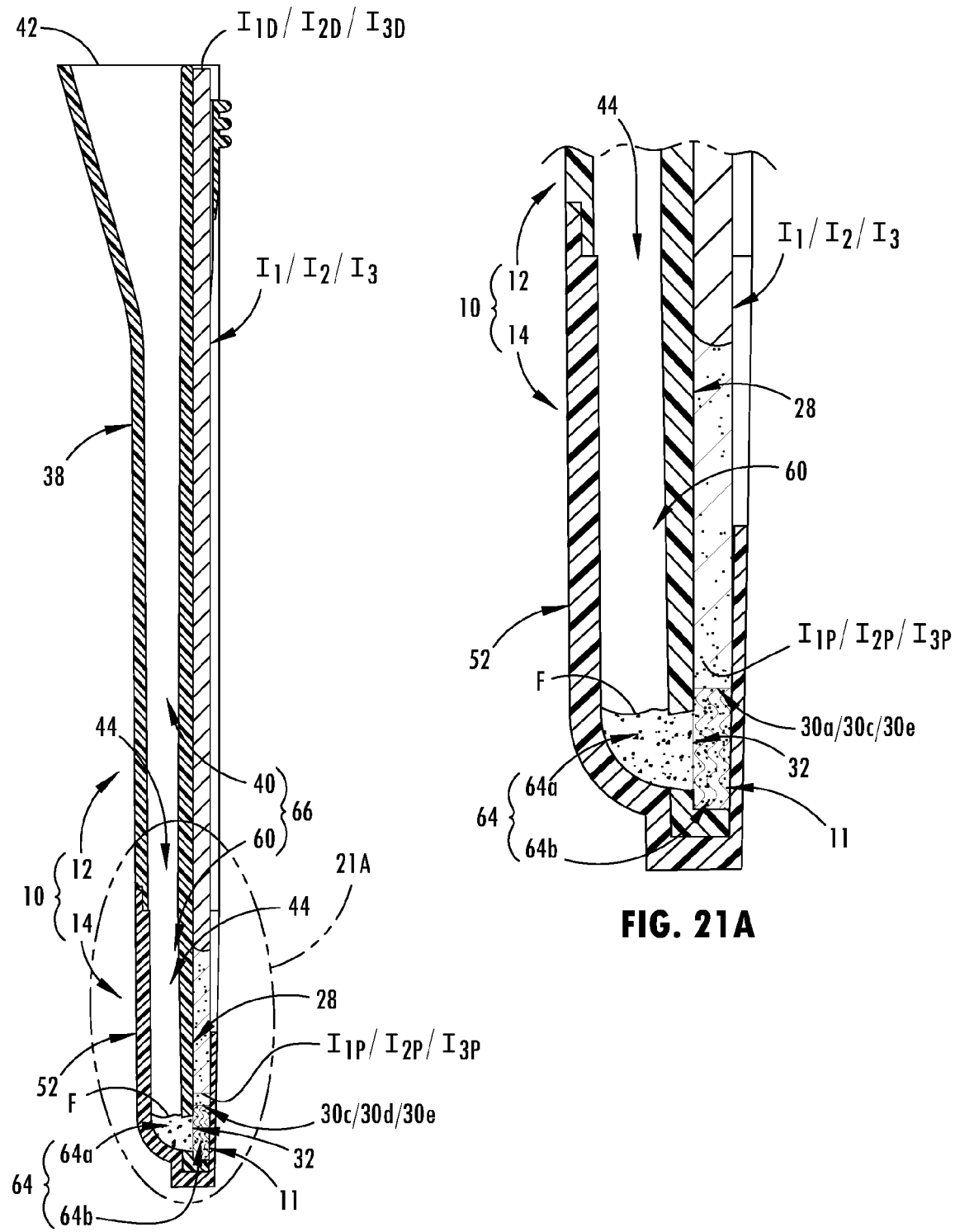
FIG. 21 is another cross-sectional view of the fluid retainer cartridge assembly according to FIG. 20.

As seen in FIGS. 21 and 21A, after the fluid F arrives in the downstream fluid-receiving void 64b of the fluid-receiving void 64 and moves around projections 30, the fluid F comes into contact with the proximal end $I_{1P}$, $I_{2P}$, $I_{3P}$ of each test strip assay $I_1$, $I_2$, $I_3$ and fluid F is drawn up each test strip assay $I_1$, $I_2$, $I_3$, for example, by capillary action. The shape, quantity and arrangement (e.g., centering along the dashed lines $C_{18a}$, $C_{18b}$, $C_{18c}$, $C_{22a}$, $C_{22b}$ of FIG. 2) of the plurality of projections 30 may assist in evenly distributing and selectively flowing the fluid F about the proximal end $I_{1P}$, $I_{2P}$, $I_{3P}$ of each test strip assay $I_1$, $I_2$, $I_3$ for adequately dosing each test strip assay $I_1$, $I_2$, $I_3$ with a sufficient amount of fluid F.

Figure 22:
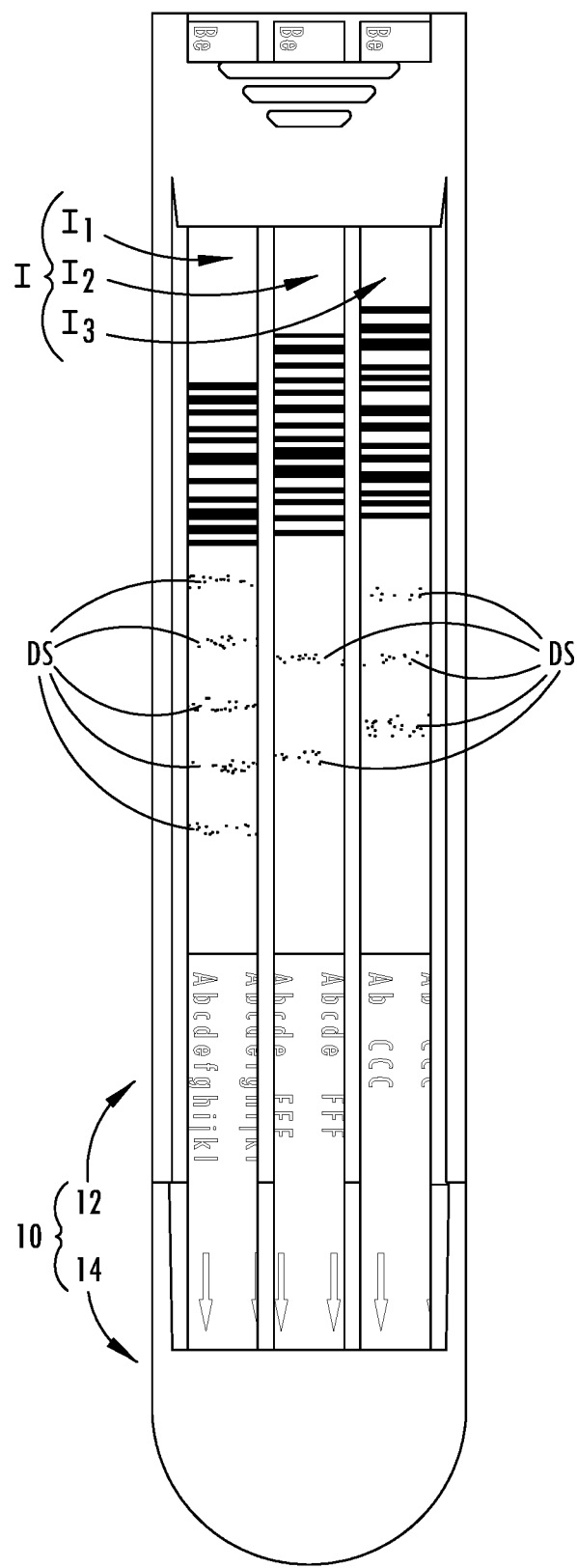
FIG. 22 is a front view of the fluid retainer cartridge assembly according to line 22 of FIG. 1B.

Referring to FIG. 22, in one use of the fluid retainer cartridge assembly 10, after being contacted with the fluid F, each test strip assay $I_1$, $I_2$, $I_3$ may provide a detectable signal DS (e.g., a color change) indicating the presence and/or concentration of a chemical analyte; and the detectable signal DS may be determined by exposing each test strip assay $I_1$, $I_2$, $I_3$ to an optical reader of an implement analyzing device (not shown) that can monitor, read and analyze the one or more test strip assays $I_1$, $I_2$, $I_3$ during or after being contacted with the fluid F. Exposure of each test strip assay $I_1$, $I_2$, $I_3$ to an optical reader of an implement analyzing device may be permitted by the fluid retainer cartridge assembly 10 forming a viewing window or viewing port 70 (see, e.g., FIG. 1B). The viewing window or viewing port 70 is defined by an absence of material of one or both of the base portion 12 and the cap portion 14. In an example, the viewing window or viewing port 70 is generally bound by: (1) the first sidewall flange 20a of the front surface $16_F$ of the body 16 of the base portion 12, (2) the second sidewall flange 20b of the front surface $16_F$ of the body 16 of the base portion 12, (3) the proximal end $24_P$ of the implement distal end retainer portion 24 the front surface $16_F$ of the body 16 of the base portion 12 and (4) the fluid overflow edge 68 formed by the front surface $52_F$ of the body 52 of the cap portion 14.

In other examples (as shown in FIGS. 7 and 13), the inner surface $38_I$ of the funnel body 38 formed by the base portion 12, the portion $52_{F-P}$ of the front surface $52_F$ that extends along the length $L_{56}$ of the implement proximal end retainer portion 56, and/or the inner surface $56_I$ of the implement proximal end retainer portion 56 may include an optional dried reagent 72 disposed thereon. Such reagents may include acids, bases, buffers, surfactants, dyes, colorometric signaling agents, fluorometric signaling agents, antibodies, enzymes, receptors, antigens, cofactors, chemical filtration agents, anticoagulants, blocking agents, chelating agents, and leaching agents.

In yet another implementation, the fluid retainer cartridge assembly 10 may include a seal 74, which may be formed from, for example, a foil material. The seal 74 may be disposed over, adjacent, proximate or near the distal surface $38_D$ of the funnel body 38. The seal 74 may serve one or more purposes, for example, to prevent contamination of the inner surface $38_I$ of the funnel body 38 and/or for retention of dried reagent 72 on the inner surface $38_I$ of the funnel body 38 of base portion 12.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A fluid retainer cartridge assembly, comprising:
    a base portion having a proximal end, a distal end, a body having a fluid-flow passage, a flange having a fluid-flow passage, and a plurality of implement-receiving channels for removably receiving implements, wherein the fluid-flow passage of the body includes an upstream opening at the distal end of the base portion; and
    a cap portion removably-connected to the proximal end of the base portion, wherein the cap portion defines a fluid-receiving void that is fluidly-divided into an upstream fluid-receiving void and a downstream fluid-receiving void by the flange of the base portion, wherein the flange of the base portion is disposed within the fluid-receiving void of the cap portion, and wherein the upstream fluid-receiving void is in fluid communication with the downstream fluid-receiving void through the fluid-flow passage of the flange of the base portion.

2. The fluid retainer cartridge assembly of claim 1 further comprising:
    a fluid filter disposed adjacent the fluid-flow passage formed by the flange of the base portion.

3. The fluid retainer cartridge assembly of claim 1, wherein
    the upstream fluid-receiving void is in fluid communication with an axial fluid conduit formed by:
        the fluid-flow passage of the body of the base portion, and
        a channel formed by the cap portion, wherein
    the downstream fluid-receiving void is in fluid communication with the plurality of implement-receiving channels.

4. The fluid retainer cartridge assembly of claim 3, wherein the plurality of implement-receiving channels are further defined by:
    a first sidewall flange extending from the front surface of the body of the base portion,
    a second sidewall flange extending from the front surface of the body of the base portion, and at least one rib extending from the front surface of the body of the base portion and arranged between the first sidewall flange and the second sidewall flange.

5. The fluid retainer cartridge assembly of claim 4, wherein the front surface of the body of the base portion further defines an implement distal end retainer portion that extends across a width of the base portion and connects the first sidewall flange to the second sidewall flange.

6. The fluid retainer cartridge assembly of claim 5, wherein the implement distal end retainer portion is defined by a distal end and a proximal end, wherein the distal end of the implement distal end retainer portion is arranged at a distance away from the distal end surface of the body of the base portion for defining an access port.

7. The fluid retainer cartridge assembly of claim 4, wherein the at least one rib includes a first rib and a second rib, wherein the first rib is arranged between the first sidewall flange and the second rib, wherein the second rib is arranged between the first rib and the second sidewall flange.

8. The fluid retainer cartridge assembly of claim 7, wherein the first sidewall flange is spaced apart from the first rib at a distance equal to a first portion of a width of the base portion for defining a first implement-receiving channel of the plurality of implement-receiving channels, wherein the first rib is spaced apart from the second rib at a distance equal to a second portion of the width of the base portion for defining a second implement-receiving channel of the plurality of implement-receiving channels, wherein the second rib is spaced apart from the second sidewall flange at a distance equal to a third portion of the width of the base portion for defining a third implement-receiving channel of the plurality of implement-receiving channels.

9. The fluid retainer cartridge assembly of claim 8, wherein the front surface of the body of the base portion defined by the flange includes a plurality of projections arranged in a row at a length away from a proximal end surface of the body of the base portion.

10. The fluid retainer cartridge assembly of claim 9, wherein the plurality of projections includes:
a first projection aligned with the first implement-receiving channel,
a second projection aligned with the first rib,
a third projection aligned with the second implement-receiving channel,
a fourth projection aligned with the second rib, and
a fifth projection aligned with the third implement-receiving channel.

11. The fluid retainer cartridge assembly of claim 1, wherein the fluid-flow passage of the body of the base portion is formed, in part, by a rear surface of the body of the base portion and is further defined by an inner surface of a funnel body that extends away from the rear surface of the body of the base portion, and wherein access to the fluid-flow passage of the body of the base portion is formed by the upstream opening and a downstream opening.

12. The fluid retainer cartridge assembly of claim 11, wherein the fluid-flow passage of the body of the base portion is defined by an arcuate channel having a radius extending between the inner surface of the funnel body and the rear surface of the base portion, wherein the radius progressively increases near a distal surface of the funnel body such that the upstream opening forms a larger opening than that of the downstream opening.

13. The fluid retainer cartridge assembly of claim 1, wherein a rear surface of the body of the base portion forms a cap-retainer portion defined by a pair of protrusions including a first protrusion and a second protrusion, wherein each of the first protrusion and the second protrusion includes a ramp surface and latch surface.

14. The fluid retainer cartridge assembly of claim 13, wherein a body of the cap portion defines a pair of protrusion-receiving passages that extend through the thickness of the body of the cap portion, wherein the pair of protrusion-receiving passages include a first protrusion-receiving passage and a second protrusion-receiving passage, wherein the first protrusion and the second protrusion are respectively arranged within the first protrusion-receiving passage and the second protrusion-receiving passage.

15. The fluid retainer cartridge assembly of claim 1, wherein the fluid-receiving void of the cap portion is further defined by a flange-receiving housing including an implement proximal end retainer portion.

16. A method, comprising:
arranging at least one implement in one implement-receiving channel of the plurality of implement-receiving channels of the fluid retainer cartridge assembly of claim 1;
pouring a fluid into the fluid-receiving void of the fluid retainer cartridge assembly such that the fluid:
firstly enters the upstream fluid-receiving void then
secondly enters the fluid-flow passage formed by the flange of the base portion of the fluid retainer cartridge assembly then
thirdly enters the downstream fluid-receiving void for fluidly contacting the fluid with the at least one implement that is in fluid communication with the downstream fluid-receiving void.

17. The method of claim 16, wherein the at least one implement is a test strip assay and the fluid includes a chemical analyte that chemically reacts with the at least one test strip assay.

* * * * *